(12) United States Patent
Tillman et al.

(10) Patent No.: US 10,278,384 B2
(45) Date of Patent: May 7, 2019

(54) ENDOVASCULAR APPARATUS FOR PERFUSING ORGANS IN A BODY

(71) Applicant: University of Pittsburgh—Of the Commonwealth System of Higher Education, Pittsburgh, PA (US)

(72) Inventors: Bryan W. Tillman, Pittsburgh, PA (US); Amit D. Tevar, Pittsburgh, PA (US); Youngjae Chun, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 343 days.

(21) Appl. No.: 15/115,623

(22) PCT Filed: Dec. 2, 2014

(86) PCT No.: PCT/US2014/068116
§ 371 (c)(1),
(2) Date: Jul. 29, 2016

(87) PCT Pub. No.: WO2015/119700
PCT Pub. Date: Aug. 13, 2015

(65) Prior Publication Data
US 2017/0164605 A1    Jun. 15, 2017

Related U.S. Application Data

(60) Provisional application No. 61/935,729, filed on Feb. 4, 2014.

(51) Int. Cl.
*A01N 1/02*     (2006.01)
*A61M 1/36*     (2006.01)
(Continued)

(52) U.S. Cl.
CPC ......... *A01N 1/0247* (2013.01); *A01N 1/0226* (2013.01); *A01N 1/0242* (2013.01);
(Continued)

(58) Field of Classification Search
CPC .. A61N 1/0247; A61N 1/0226; A61N 1/0242; A61N 1/0242; A61M 1/3659;
(Continued)

(56) References Cited

U.S. PATENT DOCUMENTS

| 5,505,701 A | 4/1996 | Anaya Fernandez de Lomana |
| 5,908,407 A * | 6/1999 | Frazee ............... A61M 25/1011 604/101.01 |

(Continued)

FOREIGN PATENT DOCUMENTS

| WO | WO 1999/004849 A1 | 2/1999 |
| WO | WO 2001/080918 A1 | 11/2001 |

(Continued)

OTHER PUBLICATIONS

Amoroso et al., "Elastomeric electrospun polyurethane scaffolds: The interrelationship between fabrication conditions, fiber topology, and mechanical properties," *Advanced materials*, 23:106-111, 2011.

(Continued)

*Primary Examiner* — Philip R Wiest
(74) *Attorney, Agent, or Firm* — Klarquist Sparkman, LLP

(57) ABSTRACT

In one representative embodiment, a method of perfusing organs in a patient's body is provided. The method comprises isolating the visceral arteries and the visceral veins from blood circulating through the patient's heart and perfusing the visceral arteries, the visceral veins, and the abdominal organs with a perfusion fluid that is fluidly separated from the blood circulating through the patient's heart. While the visceral arteries and the visceral veins are (Continued)

isolated, and the visceral arteries, the visceral veins, and the abdominal organs are being perfused, the patient's blood is allowed to continue to circulate through the heart.

28 Claims, 11 Drawing Sheets

(51) Int. Cl.
    *A61M 1/32*     (2006.01)
    *A61M 25/10*     (2013.01)
    *A61B 17/00*     (2006.01)
    *A61B 17/11*     (2006.01)

(52) U.S. Cl.
    CPC ............ *A61M 1/32* (2013.01); *A61M 1/3659* (2014.02); *A61M 25/1011* (2013.01); *A61B 2017/00575* (2013.01); *A61B 2017/00969* (2013.01); *A61B 2017/1107* (2013.01); *A61B 2017/1132* (2013.01); *A61M 2025/1095* (2013.01); *A61M 2205/36* (2013.01)

(58) Field of Classification Search
    CPC ................ A61M 1/32; A61M 25/1011; A61M 2025/1095; A61M 2025/36; A61B 2017/00969; A61B 2017/1107; A61B 2017/1132
    See application file for complete search history.

(56) References Cited

U.S. PATENT DOCUMENTS

| | | | |
|---|---|---|---|
| 6,730,118 B2 | 5/2004 | Spenser et al. | |
| 2002/0032405 A1 | 3/2002 | Sweezer | |
| 2003/0191448 A1 | 10/2003 | Swindle | |
| 2011/0282274 A1* | 11/2011 | Fulton, III | A61M 1/3403 604/28 |
| 2012/0302995 A1 | 11/2012 | Hochareon | |
| 2013/0331762 A1 | 12/2013 | Kassab et al. | |

FOREIGN PATENT DOCUMENTS

| | | |
|---|---|---|
| WO | WO 2004/028340 A2 | 4/2004 |
| WO | WO 2015/006607 A1 | 1/2015 |

OTHER PUBLICATIONS

Apfel et al., "Restoration of disk height through non-surgical spinal decompression is associated with decreased discogenic low back pain: A retrospective cohort study," *BMC musculoskeletal disorders*, 11:155, 2010.
Barrou et al., "The use of extracorporeal membranous oxygenation in donors after cardiac death," *Curr Opin Organ Transplant*, 18(2):148-53, 2013.
Bhamidipati et al., "Perfusion techniques for renal protection during thoracoabdoninal aortic surgery," *J Extra Corpor Technol*, 44(1):31-7, Mar. 2012.
Bon et al., "New strategies to optimize kidney recovery and preservation in transplantation," *Nature Reviews, Nephrology*, 1-9, May 1, 2012.
Brook et al., "Nonheart-beating kidney donation: Current practice and future developments," *Kidney International*, 63:1516-29, 2003.
Chun et al, Thin film nitinol microstent for aneurysm occlusion, *J. Biomechanical Engineering*, 131(5):051014-1-8, 2009.
Chun et al., "Modeling and experimental analysis of the hyperelastic think film nitinol," *Journal of Intelligent Material Systems and Structures*, 22:2045-51, 2011.
Chun et al., "Novel micro-patterning processes for thin film niti vascular devices," *Smart Materials and Structures*, 19:105021, 2010.
Coselli, "The use of left heart bypass in the repair of thoracoabdominal aortic aneurysms: current techniques and results," *Seminars in Thoracic and Cardiovascular Surgery*, 14(4):326-32, Oct. 2003.
Crutchley et al., "Branch renal artery repair with cold perfusion protection," *J. Vasc. Surg.* 46:405-12, 2007.
Fondevila et al., "Liver transplant using donors after unexpected cardiac death: novel preservation protocol and acceptance criteria," *AM J Transplant.* 7(7):1849-55, 2007.
Gocmen-Mas et al., "Evaluation of lumbar vertebral body and disc: A stereological morphometric study," *International Journal of Morphology*, 28:841-47, 2010.
Hong et al., Measurement of the normal lumbar intervertebral disc space using magnetic resonance imaging, *Asian spine journal*, 4:1-6, 2010.
International Search Report and Written Opinion issued by the Korean Intellectual Property Office for PCT Publication No. PCT/US2014/068116, dated Mar. 17, 2015.
Iwanaga et al., "Pancreas preservation for pancreas and islet transplantation," *Current Opinion in Organ Transplantation*, 13:445-51, 2008.
Jordan et al., "Abdominal Aortic Aneurysms in "High-Risk" Surgical Patients," *Ann Surg.*, 237(5):623-30, May 2003.
Ko et al., "Extracorporeal membrane oxygenation support of donor abdominal organs in non-heart-beating donors," *Clin Transplant*, 14:152-56, 2000.
Kohler et al., Duplex scanning for diagnosis of aortoiliac and femoropopliteal disease: A prospective study, *Circulation*, 76:1074-80, 1987.
Kootstra et al., "Non-heartbeating donation of kidneys for transplantation," *Nature Clinical Practice, Nephrology*, 3(3):154-63, Mar. 2007.
Kootstra, "The Asystolic, or Non-Heartbeating, Donor," *Transplantation*, 63(7):917-21, Apr. 15, 1997.
Magliocca et al., "Extracorporeal support for organ donation after cardiac death effectively expands the donor pool," *J Trauma*, 58:1095-1102, 2005.
Miranda et al., "Optimizing cadaveric organ procurement: the Catalan and Spanish experience," *Am J Transplant*, 3:1189-96, 2003.
Prakash et al., "The abdominal aorta and its branches: Anatomical variations and clinical implications," *Folia morphologica*, 70(4):282-86, 2011.
Reznik et al., "Kidney from uncontrolled donors after cardia death with one hour warm ischemic time: resuscitation by extracorporal normothermic abdominal perfusion "In situ" by leukocytes-free oxygenated blood," *Clin Transplant*, 25:511-16, 2011.
Rigberg et al., "Thin-film nitinol (niti): A feasibility study for a novel aortic stent graft material," *Journal of vascular surgery*, 50:375-380, 2009.
Stannard et al., Resuscitative endovascular balloon occlusion of the aorta (REBOA) as an adjunct for hemorrhagic shock, *J. Trauma*, 71(6):1869-72, Dec. 2011.
Tojimbara et al., "Improved Outcomes of Renal Transplantation from Cardiac Death Donors: A 30 Year Single Center Experience," *American Journal of Transplantation*, 7:609-17, 2007.
Valero et al., "Normothermic recirculation reduces primary graft dysfunction of kidneys obtained from non-heart-beating donors," *Transpl Int.*, 13: 303-10, 2000.
Webb et al., "Current status of transcatheter aortic valve replacement," *J Am Coll Cardiol*, 60(6):483-92, Aug. 2012.
Yokoyama et al., "Ten-year experience in the use of double balloon catheter for kidney procurement from non-heart beating donors in cadaveric kidney transplantation," *Clin. Transplant.*, 7(3):258-62, Jun. 1993 (Abstract Only), http://www.ncbi.nlm.nih.gov/pubmed/10148845, downloaded Oct. 16, 2013.

\* cited by examiner

ENDOVASCULAR APPARATUS FOR PERFUSING ORGANS IN A BODY

CROSS REFERENCE TO RELATED APPLICATIONS

This is the U.S. National Stage of International Application No. PCT/US2014/068116, filed Dec. 2, 2014, which was published in English under PCT Article 21(2), which in turn claims the benefit of priority to U.S. Provisional Application No. 61/935,729, filed Feb. 4, 2014, which is incorporated by reference in its entirety.

FIELD

The present application concerns embodiments of an endovascular apparatus for perfusing organs in a patient, such as an organ donor patient until the organs can be removed for transplant.

BACKGROUND

In the U.S., over 120,000 patients are in need of an organ transplant. It has been reported that only about 28,000 people received organ transplants organs in 2012 in the U.S. As a result, an average of 18 patients will die each day awaiting an organ transplant. Furthermore, the economic burden of kidney dialysis while awaiting transplant is significant, costing nearly $40 billion dollars a year in the U.S. alone.

Organs recovered from living donors and those donated after brain death (DBD) (also referred to as "heartbeating donation" (HBD)) represent controlled situations where organs can be carefully exposed and cooled immediately at the time of recovery. This rapid cooling allows the highest preservation of function. Donation after cardiac death (DCD) (also referred to as "non-heartbeating donation" (NHBD)) represents a growing source of organs but presents unique challenges with regard to adequately preserving organ function just prior to transplant.

Organs (e.g., kidneys) from all donor types are susceptible to warm ischemia, which is caused by reduced blood flow or the cessation of blood flow to organs and can result in significant loss of organ function. DCD donors are particularly susceptible to rather long warm ischemia times compared to DBD donors because DCD donors can experience relatively long periods of low blood pressure that is inadequate for organ perfusion prior to actual cardiac death, such as after the DCD donor is removed from life support. Needless to say, maneuvers that expedite cardiac death are prohibited. Moreover, in order to ensure that brain damage after cardiac arrest is irreversible, transplant teams must wait a predetermined time period prior to commencing the procedure for removing an organ from the DCD donor. This time period typically is referred to as a "no-touch" time period and on average is at least five minutes from the time of pronounced cardiac death. Consequently, warm ischemia times of about 10-40 minutes have been documented for DCD donors. As a result of these delays, warm ischemia can result in significant loss of organ function.

SUMMARY

The present disclosure concerns embodiments of an endovascular apparatus that can be used to perfuse the organs of a patient, for example, the organs of a donor patient until the organs can be explanted, thereby minimizing warm ischemia times. In particular embodiments, the endovascular apparatus is configured to isolate blood circulating through the heart from flowing through the visceral arteries and veins while perfusing the organs within the abdomen with a separate perfusion liquid that helps preserve organ function until explant. As such, the endovascular apparatus is particularly suited for maintaining adequate perfusion of organs in DCD donors, in which there may not be adequate blood flow to the abdominal organs prior to cardiac arrest and during the so called "no-touch" time period following cardiac arrest. The disclosed methods and apparatuses therefore can significantly increase the number of viable organs that can be made available for transplant. In alternative embodiments, the disclosed methods and apparatuses can also be used to perfuse organs in survival surgery, such as cardiac or proximal aortic repairs where prolonged cessation of blood flow poses a risk of organ damage.

In one representative embodiment, a method of perfusing organs in a patient's body is provided. The method comprises isolating the visceral arteries and the visceral veins from blood circulating through the patient's heart. The visceral arteries, the visceral veins, and the abdominal organs are perfused with a perfusion fluid that is fluidly separated from the blood circulating through the patient's heart. While the visceral arteries and the visceral veins are isolated and being perfused with a perfusion fluid, the patient's blood continues to circulate through the heart and other parts of the body.

In another representative embodiment, a method of perfusing organs in a patient's body comprises deploying a first perfusion stent in the patient's aorta and a second perfusion stent in the patient's vena cava, the first perfusion stent allowing blood from the heart to flow in a downstream direction from a location upstream of the abdominal organs to a location downstream of the abdominal organs without flowing into the visceral arteries, the second perfusion stent allowing blood to flow in a downstream direction from a location upstream of the abdominal organs to a location downstream of the abdominal organs without flowing into the visceral veins. The first perfusion stent has enlarged end portions that seal against the inner wall of the aorta and an intermediate portion defining an arterial perfusion space between the inner wall of the aorta and the outer surface of the intermediate portion, and the second perfusion stent has enlarged end portions that seal against the inner wall of the vena cava and an intermediate portion defining a venous perfusion space between the inner wall of the vena cava and the outer surface of the intermediate portion. The first perfusion conduit has an end portion that extends through one of the enlarged end portions of the first perfusion stent; and the second perfusion conduit has an end portion that extends through one of the enlarged end portions of the second perfusion stent. The perfusion fluid flows through the first perfusion conduit, through the arterial perfusion space, through the visceral arteries, through the abdominal organs, through the visceral veins, through the venous perfusion space, and into the second perfusion conduit.

In another representative embodiment, a method of perfusing organs in a patient's body comprises inserting an arterial catheter into the patient's aorta and inserting a venous catheter into the patient's vena cava. The arterial catheter has a first lumen, a second lumen, and first and second balloons spaced apart along the length of the arterial catheter. The venous catheter has a first lumen, a second lumen, and first and second balloons spaced apart along the length of the venous catheter. The method further comprises positioning the arterial catheter in the aorta such that the first balloon is upstream of the visceral arteries and the second balloon is downstream of the visceral arteries, and positioning the venous catheter in the vena cava such that the first balloon is upstream of the visceral veins and the second balloon is downstream of the visceral veins. The first and second balloons of the arterial and venous catheters are inflated, thereby isolating the visceral arteries and visceral veins from blood circulating through the patient's heart. A flow of a perfusion fluid flows into and through the second lumen of the arterial catheter, into and through the visceral arteries, the abdominal organs, and the visceral veins, and into and through the second lumen of venous catheter while blood from the heart is allowed to flow into and through the first lumen of the arterial catheter, and back into and through the first lumen of the venous catheter.

In another representative embodiment, an assembly for perfusing organs in a patient's body comprises a first perfusion stent, a second perfusion stent, a source of a perfusion fluid, a first perfusion conduit, and a second perfusion conduit. The first perfusion stent is configured to be deployed within the aorta of a patient, the first perfusion stent allowing blood from the heart to flow in a downstream direction from a location upstream of the abdominal organs to a location downstream of the abdominal organs without flowing into the visceral arteries. The second perfusion stent is configured to be deployed within the vena cava of the patient, the second perfusion stent allowing blood to flow in a downstream direction from a location upstream of the abdominal organs to a location downstream of the abdominal organs without flowing into the visceral veins. The first perfusion conduit has an inlet in fluid communication with the source of the perfusion fluid and an outlet that is configured to be in fluid communication with the visceral arteries when the first perfusion stent is deployed within the aorta. The second perfusion conduit has an inlet that is configured to be in fluid communication with the visceral veins when the second perfusion stent is deployed within the vena cava. Using the assembly, perfusion fluid can flow through the first perfusion conduit, through the arterial perfusion space, through the visceral arteries, through the abdominal organs, through the visceral veins, through the venous perfusion space, and into the second perfusion conduit.

In another representative embodiment, an assembly for perfusing organs in a patient's body comprises an arterial catheter configured to be inserted into the aorta of a patient. The arterial catheter comprises a first lumen, a second lumen, and first and second balloons spaced apart along the length of the arterial catheter. The balloons are configured to seal against the inner wall of the aorta upstream and downstream of the visceral arteries to isolate the visceral arteries from blood circulating through the patient's heart. The assembly further comprises a venous catheter configured to be inserted into the vena cava of a patient. The venous catheter comprises a first lumen, a second lumen, and first and second balloons spaced apart along the length of the venous catheter. The balloons are configured to seal against the inner wall of the vena cava upstream and downstream of the visceral veins to isolate the visceral veins from blood circulating through the patient's heart. A source of a perfusion fluid is in fluid communication with the second lumen of the arterial catheter. The first lumen of the arterial catheter is in fluid communication with the first lumen of the venous catheter to allow blood from the heart to flow into and through the first lumen of the arterial catheter, and back into and through the first lumen of the venous catheter.

In another representative embodiment, a perfusion stent implantable within a body lumen is provided. The perfusion stent comprises a radially compressible and expandable, elongated body comprising first and second end portions and an intermediate portion extending from the first end portion to the second end portion. The first and second end portions have an outer diameter greater than an outer diameter of the intermediate portion when the body is in a radially expanded state, thereby defining an annular perfusion space between the first and second end portions and around the intermediate portion. The perfusion stent also comprises a central lumen extending through the first end portion, the intermediate portion, and the second end portion, and a perfusion lumen extending at least partially through the first end portion and having a distal opening in communication with the perfusion space. When the elongated body is in the radially expanded state within the body lumen, and the first and second end portions are engaged with an inner wall of the body lumen, the central lumen is fluidly separated from the perfusion space.

In another representative embodiment, the perfusion fluid being circulated through the isolated visceral arteries, visceral veins and abdominal organs is the patient's own blood. This blood is in a fluidly separate circuit from the blood being circulated by the heart. The blood perfusing the isolated visceral arteries, visceral veins and abdominal organs can flow into and through the second lumen of the arterial catheter, into and through the visceral arteries, the abdominal organs, and the visceral veins, and into and through the second lumen of venous catheter. The venous effluent (blood from the venous catheter) can be warmed, oxygenated and/or pressurized by an external device and returned to the second lumen of the arterial catheter to repeat the cycle. Meanwhile, blood from the heart is allowed to flow into and through the first lumen of the arterial catheter, and back into and through the first lumen of the venous catheter. This provides the abdominal organs with warmed, pulsatile, oxygenated blood independent of the blood being circulated by the heart.

The foregoing and other features and advantages of this disclosure will become more apparent from the following detailed description of several embodiments which proceeds with reference to the accompanying figures.

DETAILED DESCRIPTION

The present disclosure concerns embodiments of an endovascular apparatus that can be used to perfuse the organs of a patient, such as an organ donor patient until the organs can be removed, thereby minimizing warm ischemia times. In particular embodiments, the endovascular apparatus is configured to isolate blood from the heart from flowing through the visceral arteries and veins while perfusing the organs within the abdomen with a separate perfusion liquid that helps preserve organ function until explant. As such, the endovascular apparatus is particularly suited for maintaining adequate perfusion of organs in DCD donors, in which there may not be adequate blood flow to the abdominal organs prior to cardiac arrest and during the so called "no-touch" time period following cardiac arrest.

Figure 1:
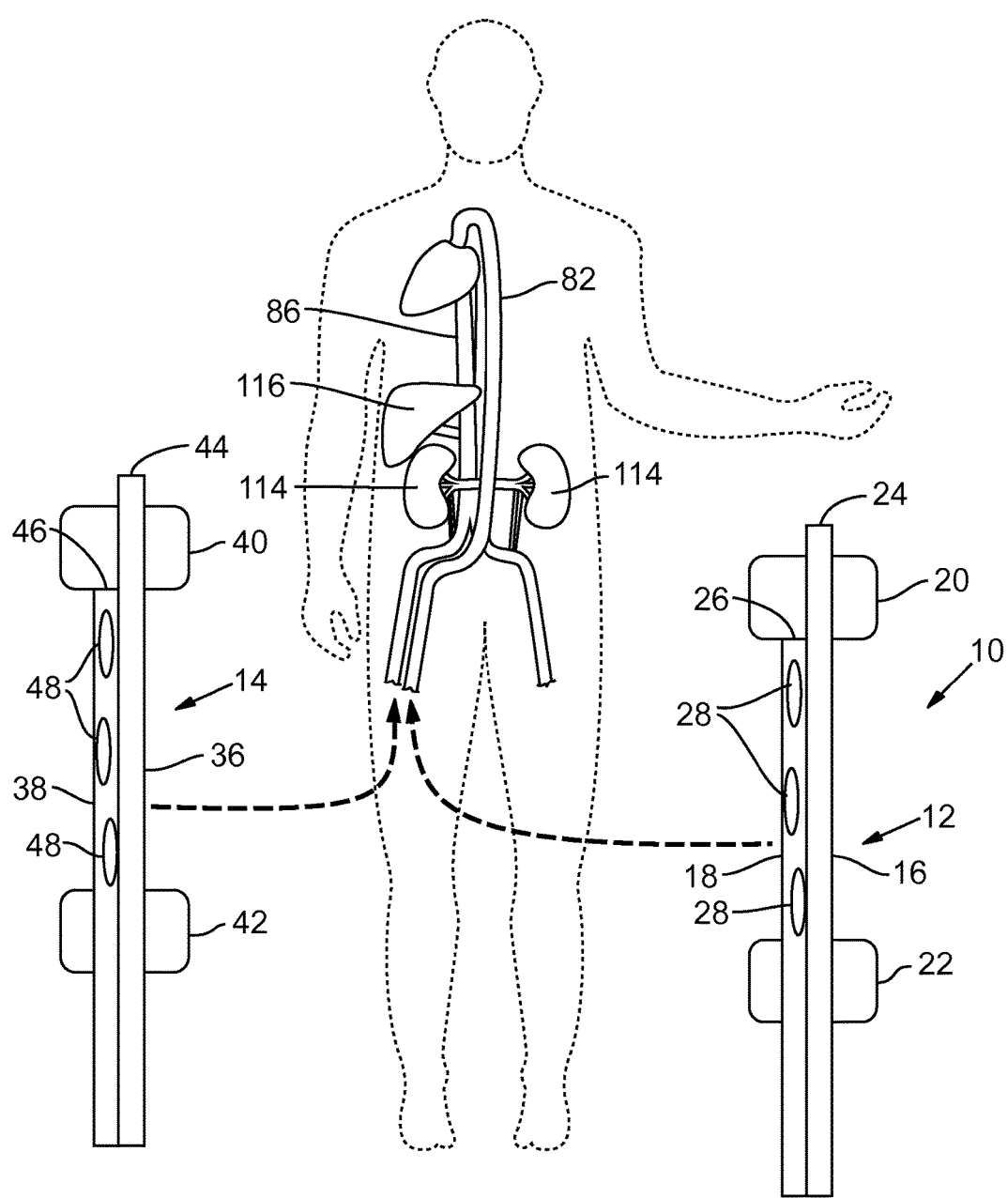
FIG. 1 illustrates an exemplary embodiment of an endovascular apparatus for perfusing organs of a patient.
Figure 2:
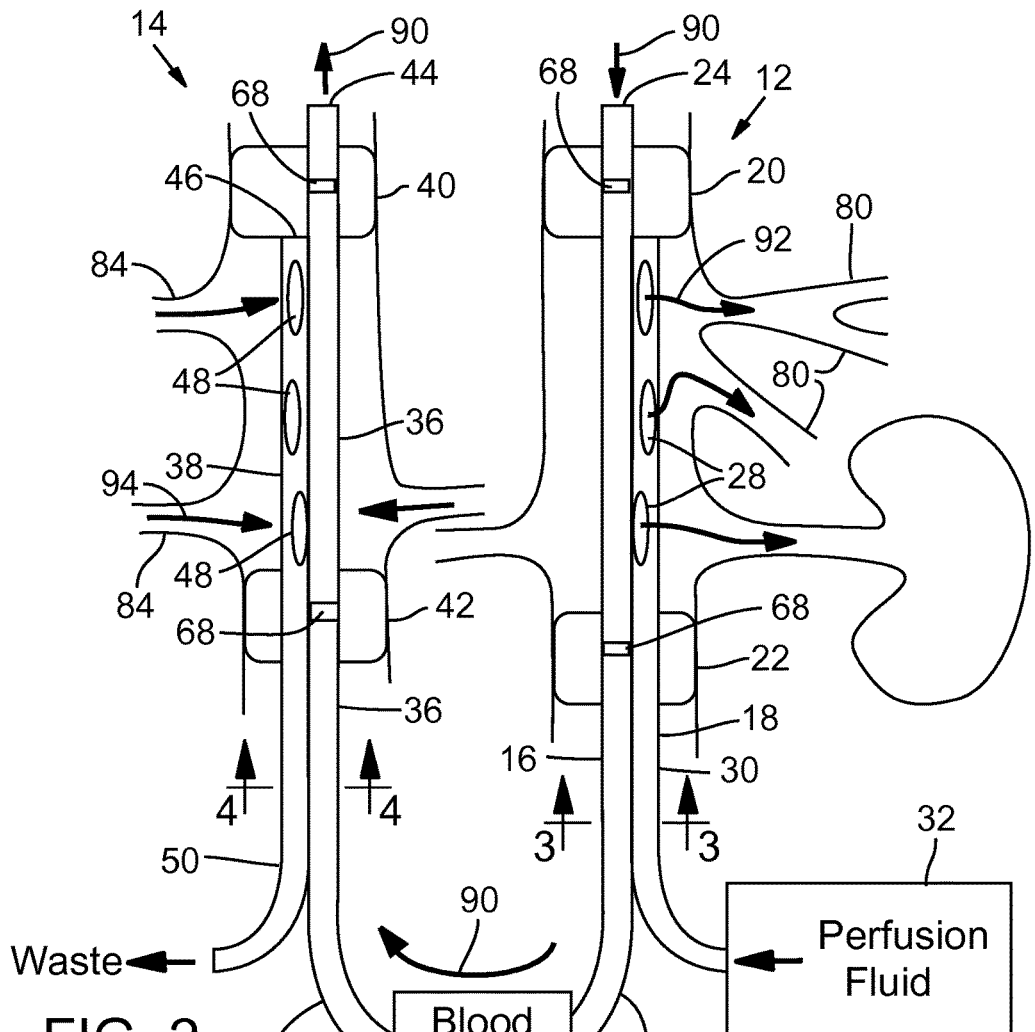
FIG. 2 is an enlarged view of the apparatus of FIG. 1, showing the apparatus deployed within the body of a patient.

Referring first to FIGS. 1 and 2, there is shown an endovascular apparatus 10 for isolating and perfusing the organs of a patient (e.g., an organ donor patient), according to one embodiment. The apparatus 10 in the illustrated embodiment comprises a first, arterial catheter 12 and a second, venous catheter 14. The arterial catheter 12 is configured to isolate the visceral arteries 80 and divert blood from the aorta 82 to a location outside the body while the venous catheter 14 is configured to isolate the visceral veins 84 and introduce the blood back into the inferior vena cava 86 of the patient. The arterial catheter 12 also is configured to introduce a perfusion fluid (e.g., a cold perfusion solution) into the visceral arteries 80 for the purpose of perfusing donor organs (e.g., kidneys 114 or liver 116) in the abdominal cavity until such time the organs can be explanted. The venous catheter 14 also is configured to be placed into fluid communication with the visceral veins 84 in order to remove the perfusion fluid from the body.

Figure 3:
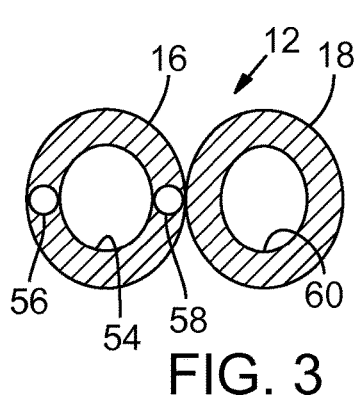
FIG. 3 is a cross-section view of the apparatus of FIG. 2 taken along line 3-3 of FIG. 2.

The arterial catheter 12 in the illustrated embodiment comprises a first shaft 16 defining a first lumen 54 (FIG. 3) and a second shaft 18 defining a second lumen 60 (FIG. 3). Mounted on the shafts 16, 18 is a distal balloon 20 and a proximal balloon 22 spaced from the distal balloon 20. As shown in FIGS. 1 and 2, the first and second shafts 16, 18 extend through the proximal balloon 22. The first shaft 16 can extend through the distal balloon 20 and has a distal opening 24 that is in fluid communication with the aorta upstream of the distal balloon. The second shaft 18 can terminate at a location proximal to the distal balloon 20 and can have a closed end 26. The second shaft 18 also can have one or more side openings, or apertures, 28 along the length of the shaft between the distal and proximal balloons 20, 22, respectively. As best shown in FIG. 2, a proximal end portion 30 of the second shaft 18 can be fluidly connected to a source 32 of a perfusion fluid. A proximal end portion 33 of the first shaft 16 can be fluidly connected to an inlet port of a blood warmer 34.

Figure 4:
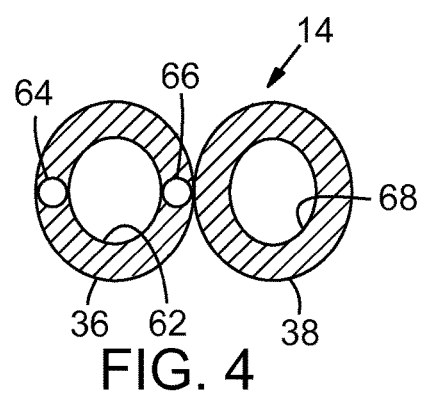
FIG. 4 is a cross-section view of the apparatus of FIG. 2 taken along line 4-4 of FIG. 2.

The venous catheter 14 in the illustrated embodiment comprises a first shaft 36 defining a first lumen 62 (FIG. 4) and a second shaft 38 defining a second lumen 68 (FIG. 4). Mounted on the shafts 36, 38 is a distal balloon 40 and a proximal balloon 42 spaced from the distal balloon 40. As shown in FIGS. 1 and 2, the first and second shafts 36, 38 extend through the proximal balloon 42. The first shaft 36 can extend through the distal balloon 40 and has a distal opening 44 that is in fluid communication with the inferior vena cava downstream of the distal balloon. The second shaft 38 can terminate at a location proximal to the distal balloon 40 and can have a closed end 46. The second shaft 38 also can have one or more side openings, or apertures, 48 along the length of the shaft between the distal and proximal balloons 40, 42, respectively. As best shown in FIG. 2, a proximal end portion 50 of the second shaft 38 can extend outside the body for draining perfusion fluid away from the body. A proximal end portion 52 of the first shaft 36 can be fluidly connected to an outlet port of the blood warmer 34.

As shown in FIG. 3, the first shaft 16 of the arterial catheter 12 can have a first lumen 54 for diverting blood from the aorta to the blood warmer 34 and second and third lumens, 56, 58, respectively, for introducing an inflation fluid to the distal and proximal balloons 20, 22, respectively. The second lumen 56 can have a distal end in fluid communication with the inside of the distal balloon 20 and a proximal end in fluid communication with a source of an inflation fluid (not shown). The third lumen 58 can have a distal end in fluid communication with the inside of the proximal balloon 22 and a proximal end in fluid communication with the source of the inflation fluid. Thus, in use, an inflation fluid (e.g., saline) can be introduced under pressure into the balloons to inflate the balloons and cause them to engage and form a seal with the inner wall of the aorta. The second shaft 18 can have a lumen 60 that allows a perfusion fluid from the source 32 to be introduced into the visceral arteries 80. In an alternative embodiment, the inflation lumens 56, 58 can be provided in the second shaft 18 rather than in the first shaft 16. In another embodiment, one of the inflation lumens can be provided in the first shaft 16 and the other inflation lumen can be provided in the second shaft 18.

As shown in FIG. 4, the first shaft 36 of the venous catheter 14 can have a first lumen 62 for introducing blood from the blood warmer 34 back into the body and second and third lumens, 64, 66, respectively, for introducing an inflation fluid to the distal and proximal balloons 40, 42, respectively. The second lumen 64 can have a distal end in fluid communication with the inside of the distal balloon 40 and a proximal end in fluid communication with the inflation fluid source. The third lumen 66 can have a distal end in fluid communication with the inside of the proximal balloon 42 and a proximal end in fluid communication with the inflation fluid source. Thus, in use, an inflation fluid (e.g., saline) can be introduced under pressure into the balloons 40, 42 to inflate the balloons and cause them to engage and form a seal with the inner wall of the inferior vena cava. The second shaft 38 can have a lumen 68 that allows the perfusion fluid returning from the visceral veins 84 to flow outside the body, where it can be collected and disposed of as waste. In an alternative embodiment, the inflation lumens 64, 66 can be provided in the second shaft 38 rather than in the first shaft 36. In another embodiment, one of the inflation lumens can be provided in the first shaft 36 and the other inflation lumen can be provided in the second shaft 38.

Each of the catheters 12, 14 can include suitable positioning markers and/or sensors at convenient locations to assist in locating the balloons of each catheter at the desired locations within the aorta and the inferior vena cava. In the illustrated embodiment, for example, the first shaft 16 of the arterial catheter 12 includes a pair of radiopaque markers 68 aligned with the distal and proximal balloons 20, 22, respectively. Similarly, the first shaft 36 of the venous catheter 14 includes a pair of radiopaque markers 68 aligned with the distal and proximal balloons 40, 42, respectively. In alternative embodiments, the markers 68 can be provided on the second shafts 18, 38 or on both the first and second shafts of each catheter 12, 14. Also, although the illustrated embodiment includes a pair of markers 68 for each catheter, a greater or fewer number of markers can be provided for each catheter 12, 14.

In alternative embodiments, the positioning markers can comprise passive or active emitters that can emit electromagnetic waves through the body and a corresponding detector or monitor can be used to receive the electromagnetic waves from the emitters and provide visual and/or audible feedback to a user indicating the position of the markers inside the body relative to external landmarks on the body. In particular embodiments, for example, the positioning markers can be emitters that can emit radiofrequency waves, such as radiofrequency identification (RFID) tags. Further details of the use of RFID tags as positioning marks are disclosed in co-pending Application No. 61/845,896, filed Jul. 12, 2013, and PCT/US2014/046224, filed Jul. 10, 2014, which are incorporated herein by reference.

In use, as depicted in FIG. 1, the first catheter 12 can be inserted into the aorta via an incision in a femoral artery in a minimally invasive manner using known techniques. Similarly, the second catheter 14 can be inserted into the inferior vena cava via an incision in a femoral vein in a minimally invasive manner. Guidewires, dilators and/or introducers can be used to help introduce and advance the catheters through the patient's vasculature, as known in the art. As best shown in FIG. 2, the arterial catheter 12 is positioned such that the distal balloon 20 is upstream of the visceral arteries 80 and the proximal balloon 22 is downstream of the visceral arteries 80. Similarly, the venous catheter 14 is positioned such that the distal balloon 40 is downstream of the visceral veins 84 and the proximal balloon 42 is upstream of the visceral veins 84. The proper positioning of the catheter 12, 14 can be accomplished by viewing the markers 68 under fluoroscopy.

Once the catheters are in place, each pair of balloons can be inflated against the inner walls of the aorta and inferior vena cava, thereby isolating the visceral arteries and veins. This causes oxygenated blood from the heart to flow through the first shaft 16 of the arterial catheter, through the blood warmer, through the first catheter 36 of the venous catheter and into the inferior vena cava where blood can flow back into the right atrium of the heart, as indicated by arrows 90. At the same time, a cold perfusion fluid from source 32 is introduced into the visceral arteries 80 via the side openings 28 in the second shaft 18 of the arterial catheter, as indicated by arrows 92. The perfusion fluid can flow through the abdominal organs, the visceral veins 84 and into the isolated region of the inferior vena cava, where it can then flow inwardly through the side openings 48 of the second catheter 38, as indicated by arrows 94. The perfusion fluid can then be removed from the body via the second catheter 38 for proper disposal.

In particular embodiments, the perfusion fluid can be similar to the University of Wisconsin solution and can comprise, without limitation, one or more of the following compounds: heparin, pentastarch, steroids, lactobionic acid, magnesium sulfate, raffinose, adenosine, allopurinol, glutathione, and potassium hydroxide. The perfusion fluid can be cooled to a temperature of about 0 degree C. to about 10 degrees C. for introduction into the body and more preferably to a temperature of about 4 degrees C. to about 6 degrees C. As an alternative perfusion fluid, blood separate from the circuit of blood being circulated by the heart can be propelled, oxygenated and warmed before being cycled continuously through the catheters, as further described below.

As noted above, the apparatus is particularly suited for use with DCD donors. In this regard, the catheters 12, 14 can be inserted and deployed (i.e., the balloons inflated to isolate the visceral arteries and veins) in the vasculature of a DCD donor as soon as possible prior to cardiac death. For example, the catheters 12, 14 can be inserted and deployed in a DCD donor just prior to or at the same time as removing the patient from life support or when the donor is experiencing unstable vital signs for normal organ blood flow. The blood flow circuit allows for normal blood flow through the body, except for those isolated regions, while awaiting expected cardiac death and during the predetermined waiting period before explant can occur. In another implementation, the catheters 12, 14 can be inserted into the DCD donor prior to cardiac death and then are deployed at the time of cardiac death. In yet another implementation, the apparatus can be inserted and deployed in a donor who expires prematurely before a donor team is ready to perform the explant procedure. In any case, during the period of time before explant can be performed, the perfusion fluid reduces warm ischemia time and preserves organ function.

In another embodiment, the catheters 12, 14 can be inserted into the aorta and the vena cava of a donor (e.g., a DCD donor) but not deployed (i.e., the balloons are not inflated) until after cardiac death or until after the predetermined waiting period. This allows for normal blood flow throughout the body until the balloons are deployed. At the prescribed time (e.g., after confirmed cardiac death), the balloons can be rapidly deployed to isolate the visceral arteries and veins and a perfusion fluid (e.g., a cold solution or blood) can be circulated through the isolated regions until explant.

In the embodiment of FIGS. 1 and 2, the catheters 12, 14 also isolate the lower extremities from the flow of blood. It has been found that humans can tolerate lower extremity ischemia for several hours. If desired, however, the apparatus 10 can be adapted to permit blood from the heart to circulate through the lower extremities.

Figure 5:
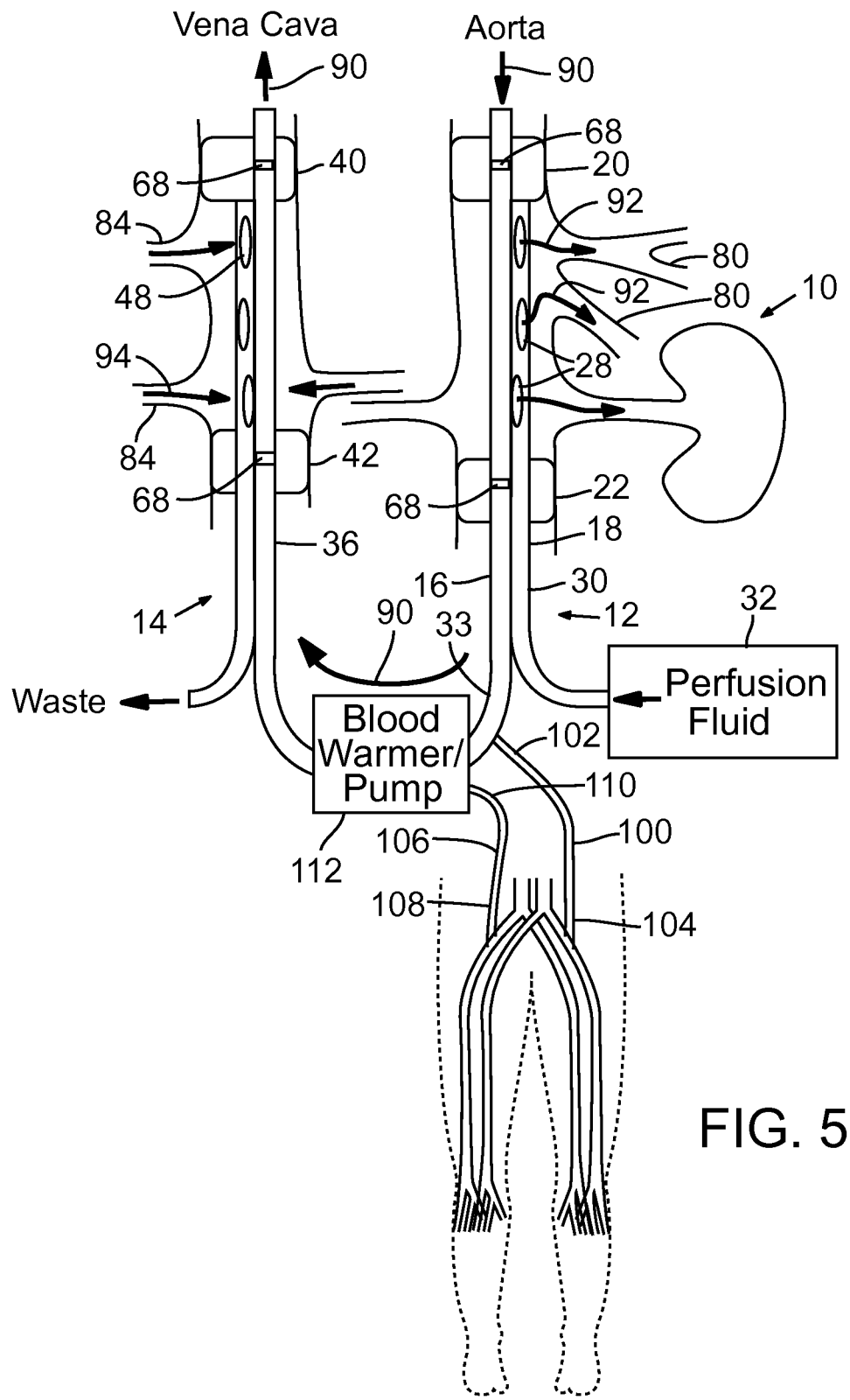
FIG. 5 illustrates another exemplary embodiment of an endovascular apparatus for perfusing organs of a patient.

For example, FIG. 5 shows the apparatus 10 of FIGS. 1 and 2 with additional components to permit blood from the heart to circulate through the lower extremities. In the embodiment of FIG. 5, the apparatus 10 further includes an arterial extension portion or conduit 100 that has a first end portion 102 that is in fluid communication with the proximal end portion 33 of the first shaft 16 of the arterial catheter 12. A second end portion 104 of the extension portion 100 can be inserted into a femoral artery, which can be the same femoral artery through which the arterial catheter 12 has been inserted or the other femoral artery. If the extension portion 100 is inserted into the same femoral artery as the arterial catheter 12, the extension portion 100 would be inserted downstream of the insertion point of the arterial catheter 12. The conduit 100 diverts a portion of blood from shaft 16 to flow into the vasculature of the lower extremities.

In the embodiment of FIG. 5, the apparatus 10 also includes a lower extremity return line or conduit 106 having a first end portion 108 inserted into a femoral vein, which can be the same femoral vein through which the venous catheter 14 has been inserted or the other femoral vein. If the return conduit 106 is inserted into the same femoral vein as the venous catheter 14, the return line would be inserted upstream of the insertion point of the venous catheter 14. A second end portion 110 of the return conduit 106 is in fluid communication with an inlet port of a blood pump 112. As shown in FIG. 5, the proximal end portion 33 of shaft 16 is also in fluid communication with a respective inlet port of the blood pump 112. In this manner, the blood flowing through the vasculature of the lower extremities is returned to pump 112 via the return conduit 106.

The blood pump 112 is configured to allow higher pressure blood from shaft 16 and lower pressure blood from return conduit 106 to mix and equalize before it is pumped under pressure into shaft 36 of the venous catheter 14. For example, the blood pump can have an internal storage chamber that receives blood from the return conduit 106 and shaft 16 at static pressure. Blood from the storage chamber can then be pumped under pressure into shaft 36. In this manner, blood from the heart can be diverted to flow through the lower extremities and back into the vena cava. Blood from shaft 16 and return conduit 106 can also flow through a blood warmer, which can be an integral or separate component from the blood pump 112.

Figures 6, 7, 8:
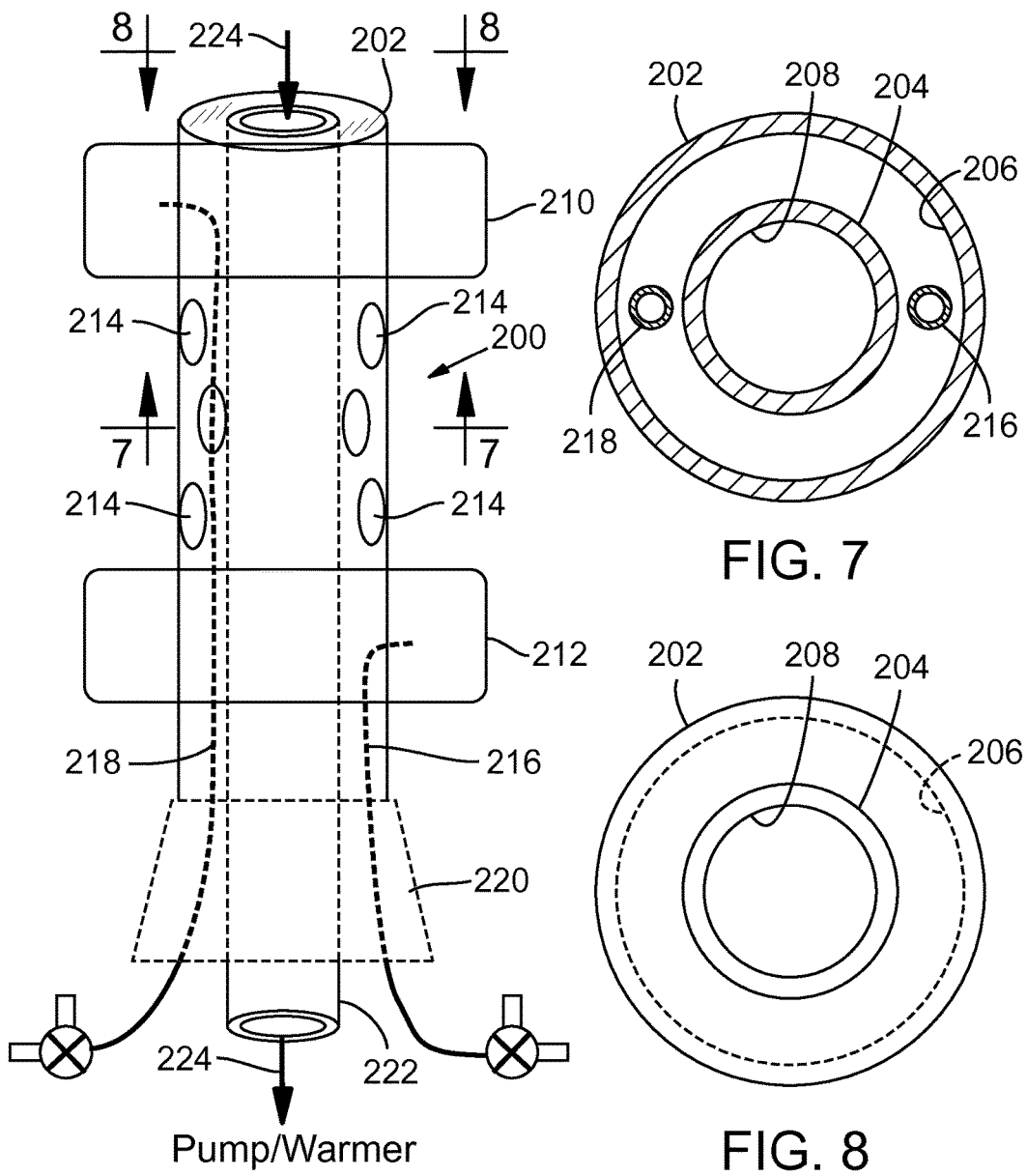
FIG. 6 is a side view of an arterial catheter of an endovascular apparatus, according to another embodiment.
FIG. 7 is a cross-section view of the apparatus of FIG. 6 taken along line 7-7 of FIG. 6.
FIG. 8 is a cross-section view of the apparatus of FIG. 6 taken along line 8-8 of FIG. 6.

FIG. 6 shows an arterial catheter 200 for an endovascular apparatus, according to another embodiment. The arterial catheter 200 performs the same function as the arterial catheter 12 of FIGS. 1 and 2 but has a different construction. The arterial catheter 200 comprises an outer shaft 202, an inner shaft 204 spaced radially inwardly from the outer shaft 202, an annular lumen 206 defined between shafts 202, 204, and an inner lumen 208 defined by the inner shaft 204. Mounted on the outer shaft 202 are two spaced apart inflatable balloons 210, 212. A plurality of side openings or apertures 214 are formed along the length of the outer shaft 202 between the balloons 210, 212. First and second inflation conduits 216, 218, respectively, extend through the annular lumen 206. The first inflation 216 conduit has a distal end that is fluid communication with the proximal balloon 212 and a proximal end that is in fluid communication with a source of an inflation fluid. The second inflation conduit 218 has a distal end that is fluid communication with the distal balloon 214 and a proximal end that is in fluid communication with the inflation fluid source.

The proximal end of the outer shaft 202 can terminate at a proximal hub 220 that extends outside the body and is fluidly connectable to a source of a perfusion fluid. The inner shaft 204 has a proximal end portion 222 that extends outside the body and is fluidly connectable to a blood warmer and/or pump (not shown in FIG. 6). The annular lumen 206 is closed at the distal end of the outer shaft 202.

The arterial catheter 200 can be inserted and deployed within a patient's aorta in the same manner described above in connection with the arterial catheter 12. A venous catheter (not shown) having the same construction as the arterial catheter 200 can be inserted into the vena cava in the same manner described above in connection with the venous catheter 14. In use, the inner shaft of the venous catheter is fluidly connected to the outlet of the blood pump/warmer and the outer shaft of the venous catheter can be fluidly connected to a drain outside the body. Upon deployment of the arterial catheter 200 and the similarly constructed venous catheter, the visceral arteries and veins are isolated and blood from the heart flows proximally through the inner lumen 208 and exits the body where it can be routed through the blood pump/warmer, as indicated by arrows 224. Blood from the blood pump/warmer can be returned to the vena cava via the inner lumen of the venous catheter where returning blood can flow back to the heart. The abdominal organs can be perfused by introducing a pressurized perfusion fluid into the annular lumen 206 of the catheter 200, which then flows outwardly through side openings 214 into the visceral arteries. The perfusion fluid can then flow through the abdominal organs, the visceral veins, and back into and through the annular lumen of the venous catheter via side openings in the venous catheter.

Figure 9:
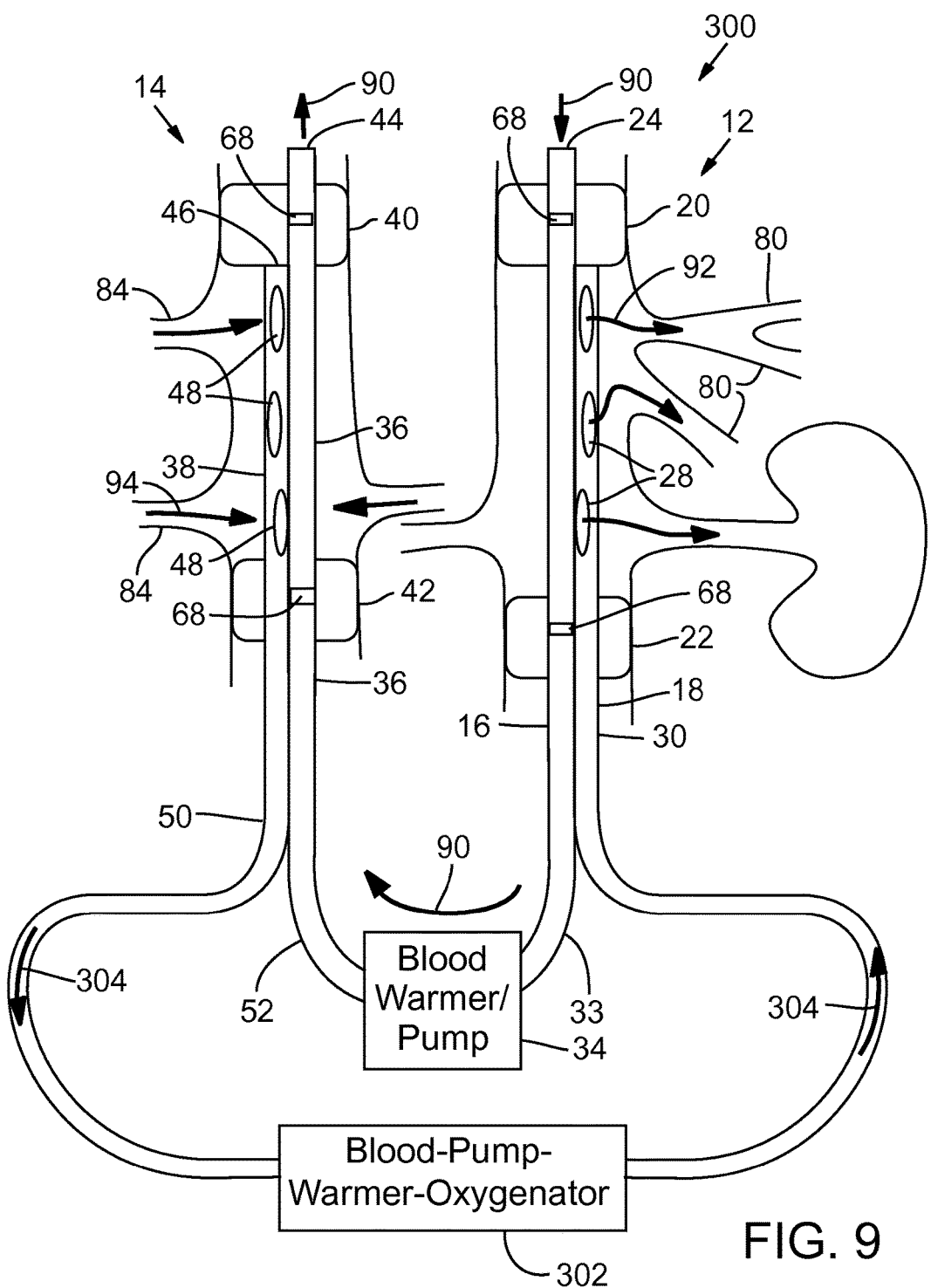
FIG. 9 illustrates another exemplary embodiment of an endovascular apparatus for perfusing organs of a patient.

FIG. 9 shows an endovascular apparatus 300, according to another embodiment. The apparatus 300 is similar in many respects to the apparatus 10 of FIGS. 1 and 2. Thus, components in FIG. 9 that are the same as components in FIGS. 1 and 2 are given the same respective reference numbers and are not described further.

In the embodiment of FIG. 9, the isolated regions of the patient's vasculature can be perfused with the patient's own blood rather than a cold perfusion solution. The apparatus 300 comprises a cardiopulmonary bypass machine 302 or equivalent device that can warm, oxygenate and pressurize blood. The machine 302 has an inlet port fluidly connected to the second shaft 38 of the venous catheter 14 and an outlet port fluidly connected to the second shaft 18 of the arterial catheter. In use, blood can be drawn from the patient and introduced into a blood flow circuit that is fluidly separated from the blood being circulated by the heart. The blood being used as the perfusion fluid is circulated outwardly from the body via the second shaft 38 of the venous catheter 14, and through the cardiopulmonary bypass machine 302, which can oxygenate and warm the blood, and pump the blood back into the body via the second shaft 18 of the arterial catheter 12, in the direction indicated by arrows 304. Maintaining blood circulation through the isolated regions that is fluidly separated from the circulation of blood through the patient's heart allows for adequate perfusion of the organs while awaiting cardiac death.

The embodiments disclosed herein can be used for procedures other than procedures for preserving organ function for explant surgery. For example, in another implementation, an endovascular apparatus (e.g., an apparatus of FIG. 1, 5 or 6) can be used to perfuse organs during survival surgery, such as cardiac or proximal aortic repairs where prolonged cessation of blood flow poses a risk of organ damage.

Figure 10:
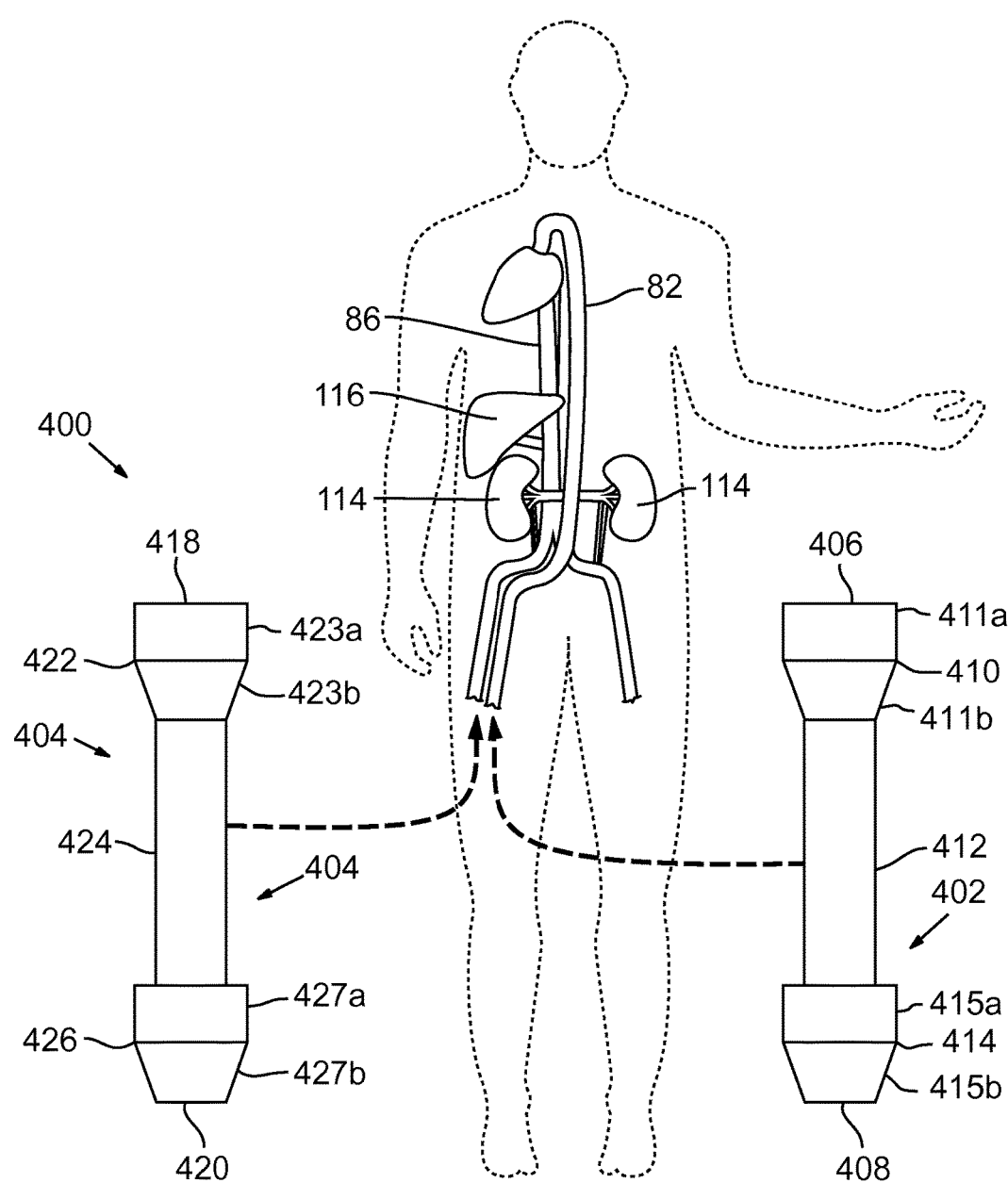
FIG. 10 illustrates an endovascular apparatus for perfusing organs of a patient, according to another embodiment.
Figure 11:
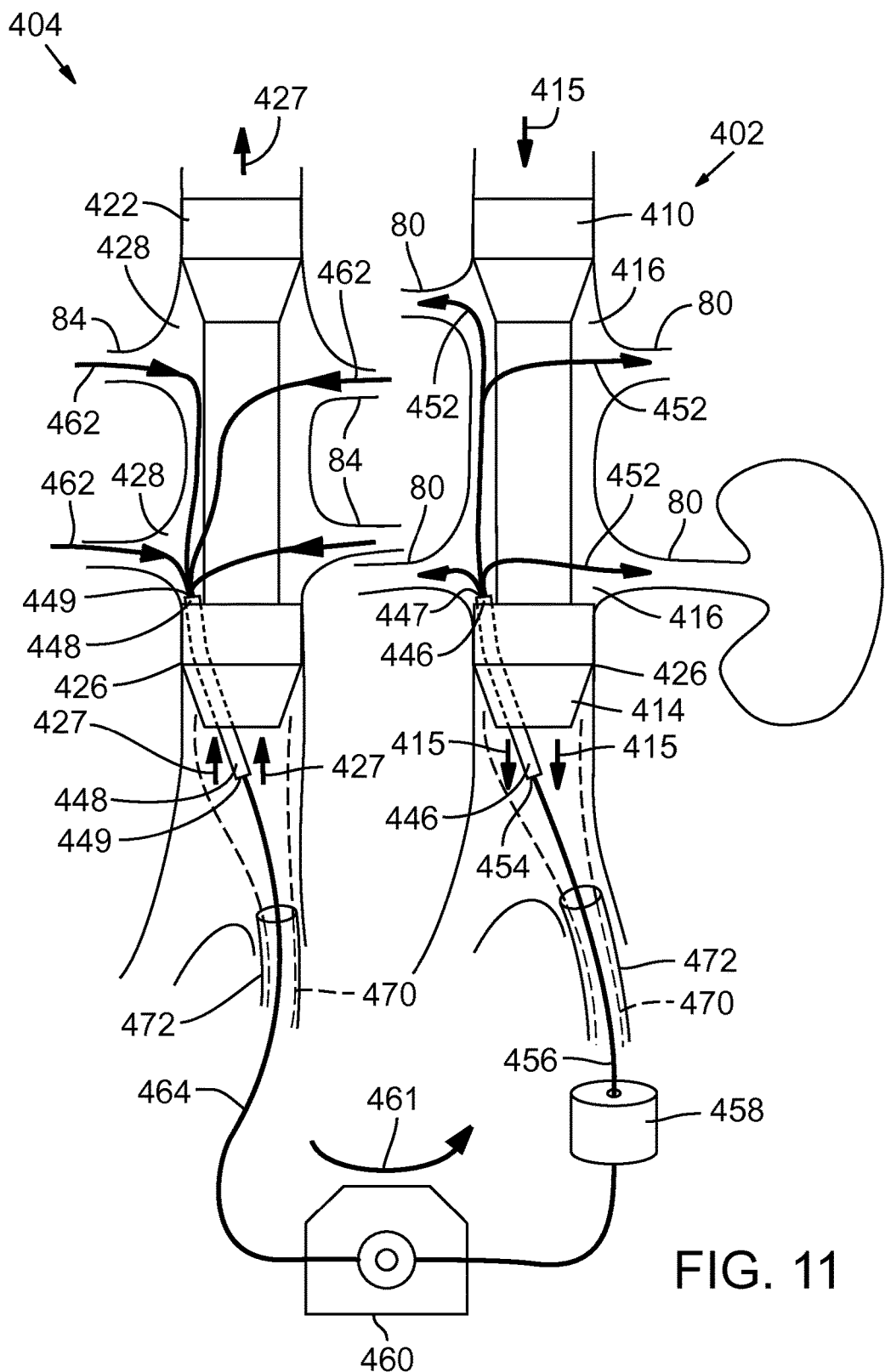
FIG. 11 is an enlarged view of the apparatus of FIG. 10, showing the apparatus deployed within the body of a patient.

Referring to FIGS. 10 and 11, there is shown another embodiment of an endovascular apparatus that can be used for isolating and perfusing the organs of a patient (e.g., an organ donor patient), indicated generally at 400. The apparatus 400 in the illustrated embodiment comprises an arterial perfusion stent 402 and a venous perfusion stent 404. The arterial perfusion stent 402 is configured to isolate blood flow to the visceral arteries 80, while allowing blood from the aorta 82 to continue to flow to the lower extremities. The venous perfusion stent 404 is configured to isolate blood flow from the visceral veins 84, while allowing blood from the lower extremities to continue to flow to the heart via the inferior vena cava 86 of the patient. Thus, when deployed in a patient, the endovascular apparatus allows blood from the heart to pass uninterrupted through a central lumen of the arterial perfusion stent 402 to perfuse the lower body and then flow through a central lumen of the venous perfusion stent 404 to return to the heart.

Additionally, the arterial perfusion stent 402 of endovascular apparatus 400 is configured to introduce a perfusion fluid (e.g., a cold perfusion solution, or re-oxygenated and/or warmed blood) into the visceral arteries 80 for the purpose of perfusing donor organs (e.g., kidneys 114 or liver 116) in the abdominal cavity until such time the organs can be explanted. The venous perfusion stent 404 is configured to receive the perfusion fluid from the visceral veins 84 that was introduced into the body from the arterial perfusion stent 402. As discussed in more detail below, the arterial and venous perfusion stents 402, 404 can each comprise a perfusion lumen (such as defined by an arterial perfusion conduit or sleeve 446 and a venous perfusion conduit or sleeve 448, see FIG. 11) that facilitates perfusion of blood or fluid through the abdominal organs, while allowing normal blood flow between the heart and lower extremities. Additionally, the arterial and venous perfusion stents 402, 404 include a non-porous liner 466 (best shown in FIG. 13) that prevents or substantially reduces mixing of blood or other fluids flowing through the aorta or inferior vena cava and the visceral arteries and veins.

Figure 13:
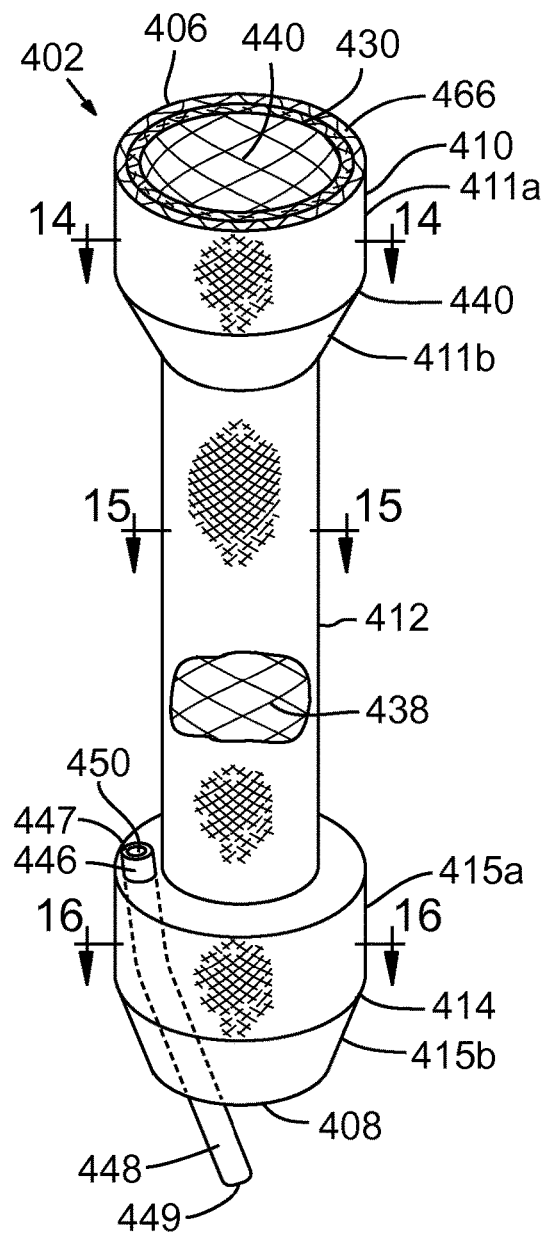
FIG. 13 is a side view of a perfusion stent, according to one embodiment.
Figure 14:
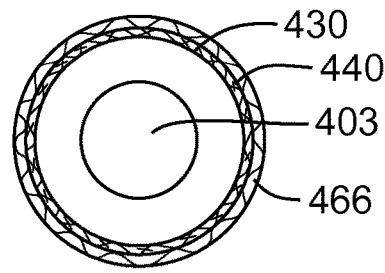
FIG. 14 is a cross-section view of the perfusion stent of FIG. 13 taken along line 13-13 of FIG. 14.
Figure 15:
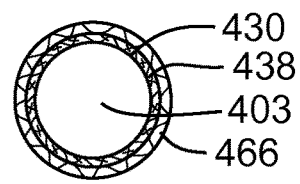
FIG. 15 is a cross-section view of the perfusion stent of FIG. 13 taken along line 14-14 of FIG. 15.
Figure 16:
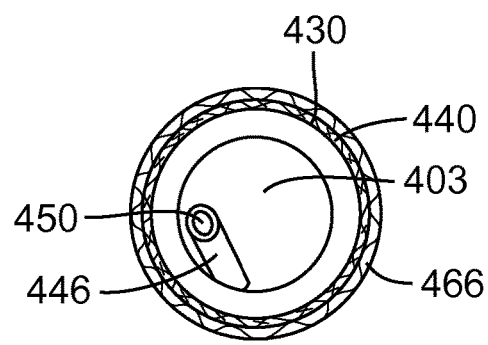
FIG. 16 is a cross-section view of the perfusion stent of FIG. 13 taken along line 15-15 of FIG. 16.

The arterial perfusion stent 402 comprises an elongated body that includes a radially compressible and expandable annular frame 430 supporting the liner 466. In FIG. 13 the frame 430 comprise a metal mesh, although the frame can have other configurations in other embodiments. Referring to FIGS. 13-16, in the illustrated embodiment, the stent 402 defines a central lumen 403 that extends from a proximal end 408 to a distal end 406 of the perfusion stent. The central lumen 403 allows passage of fluid (e.g., blood) through the body of the perfusion stent, thus maintaining blood flow through the artery in which the perfusion stent is deployed. The perfusion stent 402 can be radially compressible to a compressed state for delivery through the body to a deployment site and expandable to its functional size shown in FIG. 11 at the deployment site. In certain embodiments, the perfusion stent 402 is self-expanding; that is, the stent can radially expand to its functional size when advanced from the distal end of a delivery sheath. Apparatuses particularly suited for percutaneous delivery and implantation of a self-expanding stent in the vessels of the body are well known and described briefly below. In other embodiments, the perfusion stent can be a plastically-expandable perfusion stent that can be adapted to be mounted in a compressed state on the balloon of a delivery catheter or another type of expansion device configured to expand the stent radially from a compressed delivery state to a radially expanded state. The perfusion stent can be expanded to its functional size at a deployment site by inflating the balloon of a balloon catheter, as known in the art.

The elongated body of the arterial perfusion stent 402 comprises a distal end portion 410, a generally cylindrical intermediate portion 412, and a proximal end portion 414. The distal end portion 410 can comprise a generally cylindrical first section 411*a* and a tapered second section 411*b* positioned proximal to the first section 411*a*. Likewise, the proximal end portion 414 can comprise a generally cylindrical first section 415*a* and a tapered second section 415*b* proximal to the first section 415*a*. In the radially expanded state of the perfusion stent, the distal and proximal end portions 410, 414 have an outer diameter that is larger than the outer diameter of the intermediate portion 412, thereby defining an annular perfusion space 416 (best shown in FIG. 11) between the end portions and around the intermediate portion. Central lumen 403 extends through body of the arterial perfusion stent, allowing flow of fluid (e.g., blood) through from the distal end 406 to the proximal end 408 of the arterial perfusion stent, in the direction of arrows 415 shown in FIG. 11.

The outer surfaces of the distal and proximal end portions 410, 414 form a seal against the inner wall of the aorta when the arterial perfusion stent is in the radially expanded state. Thus, the outer surface of the distal and proximal end portions 410, 414 of the stent in the radially expanded state can have a diameter that is about the diameter of the inner surface in the region of the aorta where the stent will be placed. For example, for a perfusion stent to be placed in an adult, the outer surface of the distal and proximal end portions 410, 414 of the stent in the radially expanded state can have a diameter ranging from 12 mm to 3 cm. Smaller stents can be used in pediatric patients.

The venous perfusion stent 404 can have the same construction as the arterial perfusion stent 402. Thus, in the illustrated embodiments, the venous perfusion stent 404 has a distal end 418 and a proximal end 420. The stent 404 can comprise a distal end portion 422, a generally cylindrical intermediate portion 424, and a proximal end portion 426. The distal end portion 422 can comprise a generally cylindrical first section 423*a* and a tapered section 423*b* positioned proximal to the first section 423*a*. Likewise, the proximal end portion can comprise a generally cylindrical first section 427*a* and a tapered second section 472*b* positioned proximal to the first section 427*a*. In the radially expanded state of the venous perfusion stent, the distal and proximal end portions 422, 426 have an outer diameter that is larger than the outer diameter of the intermediate portion 424, thereby defining an annular perfusion space 428 (best shown in FIG. 11) between the end portions and around the intermediate portion. A central lumen extends through body of the venous perfusion stent, allowing flow of fluid (e.g., blood) through from the proximal to distal end of the venous perfusion stent, in the direction of arrows 427 shown in FIG. 11.

The outer surfaces of the distal and proximal end portions 422, 426 form seals against the inner wall of the inferior vena cava when the venous perfusion stent is in the radially expanded state. Thus, the outer surface of the distal and proximal end portions 422, 426 of the stent in the radially expanded state can have a diameter that is about the diameter of the inner surface in the region of the inferior vena cava where the stent will be placed. For example, for a perfusion stent to be placed in an adult, the outer surface of the distal and proximal end portions 422, 426 of the stent in the radially expanded state can have a diameter ranging from 15 mm to 3 cm. Smaller stents can be used in pediatric patients.

Figure 12:
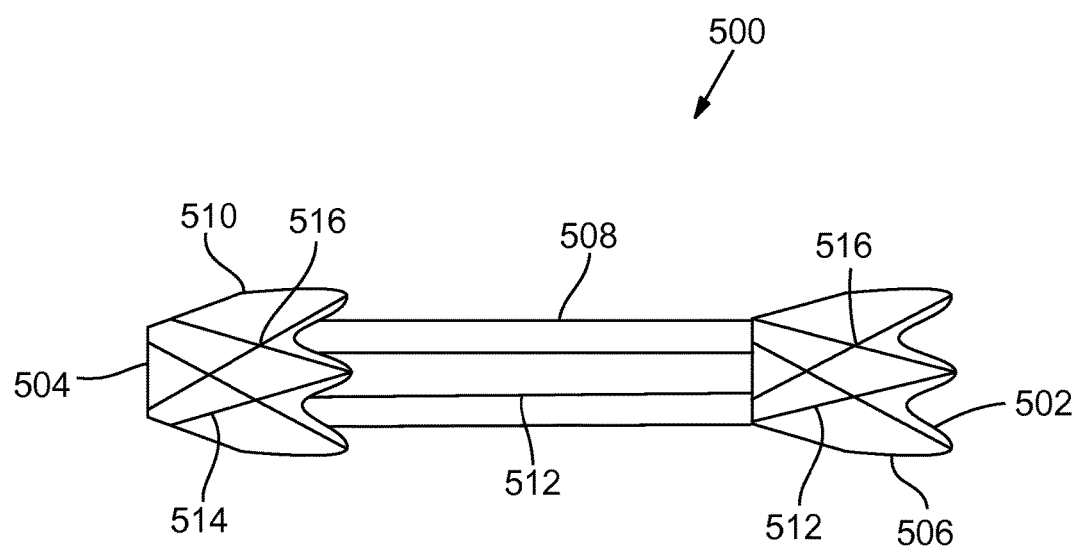
FIG. 12 is a side view of an annular frame of a perfusion stent, according to one embodiment.

FIG. 12 shows an alternate embodiment of an expandable annular frame indicated generally at 500 that can be used for the perfusion stent 402 or the perfusion stent 404. As shown, the frame 500 has a distal end 502 and a proximal end 504. The frame 500 can comprise an enlarged distal end portion 506, a generally cylindrical intermediate portion 508, and an enlarged proximal end portion 510. In the radially expanded state of the perfusion stent, the distal and proximal end portions 506, 510 have an outer diameter that is larger than the outer diameter of the intermediate portion 508. The intermediate portion 508 can be formed from a plurality of longitudinally extending frame members, or struts, 512. The distal and proximal end portions 506, 510 can be formed from angled struts 514 that are welded or otherwise secured to each other at nodes 516 formed from the vertices of adjacent bends so as to form a mesh structure.

The struts 512, 514 of the distal, intermediate, and proximal portions of the perfusion stent can be made of a suitable shape memory material, such as the nickel titanium alloy known as Nitinol, that allows the prosthetic valve to be compressed to a reduced diameter for delivery in a delivery apparatus (such as described below) and then causes the perfusion stent to expand to its functional size inside the patient's body when deployed from the delivery apparatus. If the perfusion stent is a balloon-expandable perfusion stent that is adapted to be crimped onto an inflatable balloon of a delivery apparatus and expanded to its functional size by inflation of the balloon, the perfusion stent 402 can be made of a suitable plastically expandable material, such as stainless steel.

The distal, intermediate, and proximal portions 506, 508, 510 can be constructed as a single unit, such as by machining (e.g., laser cutting). Alternatively, the frame can be constructed of separate segments each comprising respective struts or frame members, and each segment can be welded or otherwise secured together using means known in the art. In one example, the distal, intermediate, and proximal portions 506, 508, 510 are each constructed separately and secured together.

As shown in FIG. 12, the distal end portion 506 of the frame 500 in its radially expanded state can have a cylindrical shape at its distal aspect and can gradually decrease in diameter to the diameter of the intermediate portion 508. The proximal end of the distal end portion of the frame 500 is secured to the distal end of the intermediate portion 508 of the frame 430. The intermediate portion 508 of the frame in its radially expanded state generally has a uniform cylindrical shape having a diameter that is narrower than the outermost diameter of the distal and proximal end portions 436, 440 of the frame 500. The proximal end of the intermediate portion of the frame 500 is secured to the proximal end portion 510 of the frame 500. The proximal portion 510 of the frame 500 in its radially expanded state can have a cylindrical shape at its distal aspect and can gradually decrease to a narrower diameter at its proximal end, for example, to the diameter of the intermediate portion 508. The tapered proximal sections of the distal end portion 506 and the proximal end portion 510 can facilitate re-sheathing and recapture of the stent, as further discussed below.

Although a particular shape for the frame 500 is shown in FIG. 12, any shape that allows for delivery of the perfusion stent to appropriate vessel location in the patient and for formation of a seal against the inner wall of the aorta and isolation of blood flow from the aorta to the visceral arteries can be used.

The venous perfusion stent 404 can also include an expandable annular frame, which can be substantially identical to frame 500 of the arterial perfusion stent. However, the frames of the arterial and venous perfusion stents 402, 404 can include minor structural differences (for example in the diameter or length of the perfusion stent) as needed for the placement and fit of the stents when implanted in to the aorta or inferior vena cava of the patient, respectfully.

Referring to FIG. 11, the arterial perfusion stent 402 comprises a perfusion conduit 446 that facilitates perfusion of blood or other perfusion fluid to the abdominal organs in the direction of arrows 452. The arterial perfusion conduit 446 comprises an outlet 447 that opens into the arterial perfusion space 416. The perfusion fluid can flow through a perfusion lumen 450 (FIG. 16) of the arterial perfusion conduit 446 into the arterial perfusion space 416. The arterial perfusion conduit 446 can extend at least partially through the proximal end portion 414 of the stent body and has a proximal end that can extend beyond the proximal end portion 414, where it can be fluidly connected to a catheter 456 that extends outside of the body of the patient. Desirably, the catheter 456 can be connected to an oxygenator and/or blood warmer 458 and/or a blood pump 460. The oxygenator can add oxygen to the blood or other fluid flowing through the catheter, and the pulsatile pump can push blood flow in the direction of arrow 461 through the endovascular apparatus 400 and the abdominal organs of the patient.

The arterial perfusion conduit 446 can be placed anywhere in the stent body that allows the perfusion lumen 450 to be in fluid communication with the arterial perfusion space 416. In the illustrated embodiment, the arterial perfusion conduit extends from the interior of the proximal end portion 414 of the stent body to the arterial perfusion space 416, thereby allowing such access.

The venous perfusion stent 404 comprises a perfusion conduit 448 that facilitates perfusion of the perfusion fluid from the abdominal organs in the direction of arrows 462. The venous perfusion conduit 448 comprises an inlet 449 at its distal end that opens into the venous perfusion space 428. The perfusion fluid can flow from the venous perfusion space 428 and into a perfusion lumen of the venous perfusion conduit 448. The venous perfusion conduit 448 can extend at least partially through the proximal end portion 426 of the stent body and has a proximal end that can extend beyond the proximal end portion 426, where it can be connected to a catheter 464 that extends outside of the body of the patient and connects to the blood pump 460 (as shown) and/or the oxygenator and/or blood warmer 458.

The venous perfusion conduit 448 can be placed anywhere in the stent body that allows the perfusion lumen of the venous perfusion conduit 448 to be in fluid communication with the venous perfusion space 428. In the illustrated embodiment, the venous perfusion conduit extends from the interior of the proximal end portion 4426 of the arterial perfusion stent 404 to the venous perfusion space 428, thereby allowing such access.

Referring again to FIG. 13, as noted above the arterial perfusion stent 402 can include a liner 466 that is non-porous to the perfusion fluid (blood, in the illustrated embodiment). The liner can be secured to the frame 430 by any suitable means, for example an adhesive or suturing. The liner covers the frame 430 of the arterial perfusion stent and prevents or substantially reduces mixing of blood flowing through the aorta and the central lumen 403 with the perfusion fluid flowing through the perfusion space 416. The venous perfusion stent 404 includes a non-porous liner that can be substantially identical to the liner used for the arterial perfusion stent, and that prevents or substantially reduces mixing of blood flowing through the inferior vena cava with the perfusion fluid flowing through the perfusion space 428. However, the liners of the arterial and venous perfusion stents 402, 404 can include minor structural differences (for example in diameter or length) as needed for sufficient coverage of the arterial and venous perfusion stents. In the illustrated embodiment, the liner is located on the outside of the frame of the perfusion stent. However, the liner can be located on the stent in any way that provides a non-porous barrier to blood. For example, the liner can be located on the inside of the frame of the stent, or on both the outside and the inside of the stent.

In several embodiments, the liner 466 can be made of any suitable bio-compatible synthetic or biological material, such as those described in U.S. Pat. No. 6,730,118, which is incorporated herein by reference. The liner 466 desirably can be substantially impermeable to aqueous solutions, such as blood or plasma. In some embodiments, the liner 466 can be a polymer or composite membrane or layer, for example, polytetrafluoroethylene (PTFE); or a woven, knit, or non-woven fabric material (e.g., a ripstop fabric) manufactured from natural and/or synthetic yarns or fibers, such as woven polyester (e.g., polyethylene terephthalate, PET, such as Dacron®), or cellulose (such as cotton or linen), silk, nylon, polyolefin, carbon fiber, and/or metal fibers. In additional embodiments, the liner 466 can be made of a synthetic and/or natural material that is coated with a sealant (such as ePTFE, fluoropolymer, or gelatin (Vasutek® Gelatin Sealant, Terumo, UK); see, e.g., International Publication No. WO 2001/080918, which is incorporated by reference herein in its entirety). In more embodiments, the liner 466 can be made of a bio-synthetic materials and composites (e.g., collagen-polyester composites, Omniflow®, Bio Nova, Melbourne, AU). Other embodiments use natural tissue, including intestinal submucosa, natural blood vessels (arteries or veins, e.g., from animal sources), pericardial tissue and the like, which may be fixed (for example, using gluteraldehyde and/or formaldehyde). Other embodiments include artificial collagen or cellulose tubes.

In some embodiments, the liner 466 is manufactured from sheet stock, two edges of which are brought together, for example, overlapped and/or abutted, and sealed or closed to form a tube comprising a seam. In some embodiments, the seam is linear, for example, extending along a longitudinal axis. In other embodiments, the seam has a different shape, for example, zig-zag or helical. The edges are closed using any suitable method, for example, suturing, welding, gluing, laminating, and/or bonding. In other embodiments, the liner 466 does not comprise a seam, for example, when the tubular sealing member comprises a portion of a blood vessel, intestinal submucosa, or certain artificial tubular structures.

In additional embodiments, the liner 466 can desirably be made of an electrospun polyurethane fabric (see, e.g., Amoroso et al., Elastomeric electrospun polyurethane scaffolds: The interrelationship between fabrication conditions, fiber topology, and mechanical properties. *Advanced materials.* 23:106-111, 2011, which is incorporated by reference herein in its entirety). In particular embodiments, the frame 430 of the stent can comprise a micro-pattered thin Nitinol film (see, e.g., WO2004/028340; Chun et al., Thin film nitinol microstent for aneurysm occlusion, *J. Biomechanical Engineering,* 131(5):051014, 8 pages, 2009; Chun et al., Novel micro-patterning processes for thin film niti vascular devices *Smart Materials and Structures,* 19:105021, 2010; Chun et al., Modeling and experimental analysis of the hyperelastic thin film nitinol, *Journal of Intelligent Material Systems and Structures.* 22, 2045-2051, 2011; Rigberg et al., Thin-film nitinol (niti): A feasibility study for a novel aortic stent graft material *Journal of vascular surgery,* 50:375-380, 2009; each of which is incorporated by reference herein in its entirety). Micro-fabrication techniques can be used to form a plurality of micro-openings or apertures in a thin sheet of Nitinol (about 6 μM) so as to form a thin film lattice or mesh. A layer of non-porous material, such as polyurethane or ePTFE, can be applied to and secured to the metal film to provide the liner 466.

Figure 17:
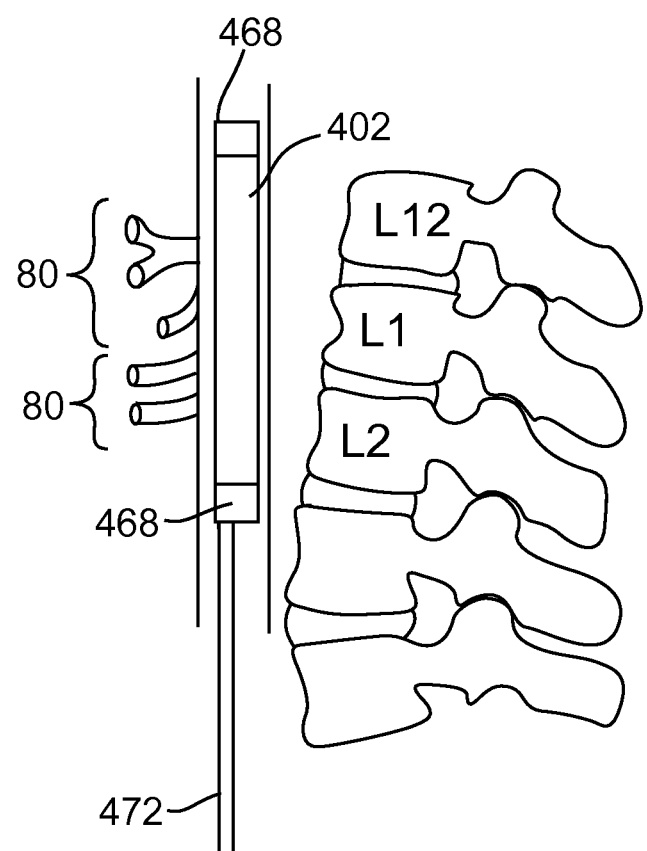
FIG. 17 shows a delivery apparatus being used to deliver a perfusion stent within the aorta of a patient.

FIG. 17 depicts the stent 402 being deployed from a sheath 472 of a delivery apparatus. As shown, each of the perfusion stents 402, 404 can include suitable positioning markers and/or sensors at convenient locations to assist in locating the proximal and distal end portions of each perfusion stent at the desired locations within the aorta or the inferior vena cava. For example, each of the distal end portion 410 and proximal end portion 414 of the arterial perfusion stent 402 can include a respective positioning marker 468 (see FIG. 17). In some embodiments, the positioning markers 468 can be radiopaque markers that can be used to locate the position of the stent during deployment in a patient by radiography. For example, an x-ray image of the stent within the body of the patient can be obtained using a bed-side x-ray machine to determine the position of the stent within the aorta or inferior vena cava. Certain bones or other tissue visible under x-ray can be used as landmarks to help position the stent relative to the visceral arteries. For example, the radiopaque markers 468 can be positioned above and below the T12 and L2 vertebrae. Although the illustrated embodiment includes a pair of positioning markers for the arterial perfusion stent, a greater or fewer number of markers can be provided as needed for the surgeon to properly position the stent in the aorta of the patient. The distal end portion 422 and proximal end portion 426 of the venous perfusion stent 404 similarly can include a corresponding pair of radiopaque markers that can be used to position the venous perfusion stent in a patient by radiography.

In an alternative embodiment, positioning markers 468 can be provided on the sheath 472. When the stent 402 is located in the sheath, one marker is aligned with the distal end portion 410 of the stent and the other marker is aligned with the proximal end portion 414.

In alternative embodiments, the positioning markers can comprise passive or active emitters that can emit electromagnetic waves through the body and a corresponding detector or monitor can be used to receive the electromagnetic waves from the emitters and provide visual and/or audible feedback to a user indicating the position of the markers inside the body relative to external landmarks on the body. In particular embodiments, for example, the positioning markers can be emitters that can emit radiofrequency waves, such as radiofrequency identification (RFID) tags. Further details of the use of RFID tags as positioning marks are disclosed in co-pending Application No. 61/845,896, filed Jul. 12, 2013, which is incorporated herein by reference.

Referring to FIG. 11, the arterial and venous perfusion stents can be secured to respective one or more recovery wires 470. The recovery wires 470 can be secured to the proximal end of the frame of the perfusion stents and can extend proximally from the perfusion stents to outside the patient's body via the artery or vein through which the perfusion stent was deployed. If it is desired to re-position or remove the arterial and/or venous perfusion stents from the patient (for example, if the patient recovers), then tension can be applied to the recovery wires to retract the perfusion stents in the proximal direction into respective sheaths 472. Once the stents are retracted into the sheaths 472, the sheaths can be withdrawn from the body. The tapered sections 411b, 415b of the end portion of the stent facilitate recapture of the stent back into the sheath 472.

In use, as depicted in FIG. 10, the arterial perfusion stent 402 can be inserted into the aorta via an incision in a femoral artery in a minimally invasive manner using known techniques. Similarly, the venous perfusion stent 404 can be inserted into the inferior vena cava via an incision in a femoral vein in a minimally invasive manner. Guidewires, dilators and/or introducers can be used to help introduce and advance the perfusion stents through the patient's vasculature, as known in the art. As best shown in FIG. 11, the arterial perfusion stent is positioned such that the distal end portion 410 is upstream of the visceral arteries 80 and the proximal end portion 414 is positioned downstream of the visceral arteries 80. Similarly, the venous perfusion stent 404 is positioned such that the distal end portion 422 is positioned downstream of the visceral veins 84 and the proximal end portion 426 is positioned upstream of the visceral veins 84. The proper positioning of the perfusion stent 402, 404 can be accomplished by viewing the markers 468 by x-ray or under fluoroscopy, for example.

Once the arterial and venous perfusion stents are in place, the proximal and distal end portions of each stent form a seal against the inner walls of the aorta and inferior vena cava, respectively, thereby isolating blood flow from the aorta 82 to the visceral arteries 80 and from the visceral veins 84 to the inferior vena cava 86. Thus, blood from the heart can flow through the arterial stent 402 (bypassing the visceral arteries), through the vasculature of the lower extremities, through the venous stent 404 (bypassing the visceral veins), and back to the heart. The blood flow to and from the visceral organs is redirected from the venous perfusion space 428 around the venous perfusion stent 404 through the venous perfusion conduit 448 and via the catheter 464 to the blood pump 460, blood oxygenator and/or warmer 458 that are outside the patient's body. The blood is then redirected back into the patient via the catheter 456 connected to the arterial perfusion conduit 446 and into the arterial perfusion space 416 around the arterial perfusion stent 402. The blood flows through the visceral arteries 80 to the abdominal organs, and back to venous perfusion space 428 via the visceral veins 84.

Although perfusion with the patient's blood is discussed above, use of a cold perfusion fluid is also available. The cold perfusion fluid can be introduced into the arterial perfusion space 416 via the arterial perfusion conduit 446, and retrieved from the venous perfusion space via the venous perfusion conduit 448 similar to that shown in FIG. 2.

In particular embodiments, the perfusion fluid can be similar to the University of Wisconsin solution and can comprise, without limitation, one or more of the following compounds: heparin, pentastarch, steroids, lactobionic acid, magnesium sulfate, raffinose, adenosine, allopurinol, glutathione, and potassium hydroxide. The perfusion fluid can be cooled to a temperature of about 0 degree C. to about 10 degrees C. for introduction into the body and more preferably to a temperature of about 4 degrees C. to about 6 degrees C. As an alternative perfusion fluid, blood separate from the circuit of blood being circulated by the heart can be propelled, oxygenated and warmed before being cycled continuously through the catheters, as further described below.

The apparatus 400 is particularly suited for use with DCD donors. In this regard, the perfusion stent 402, 404 can be inserted and deployed in the vasculature of a DCD donor as soon as possible prior to cardiac death. For example, the perfusion stent 402, 404 can be inserted and deployed in a DCD donor just prior to or at the same time as removing the patient from life support or when the donor is experiencing unstable vital signs for normal organ blood flow. The blood flow circuit allows for normal blood flow through the body, except for those isolated regions, while awaiting expected cardiac death and during the predetermined waiting period before explant can occur. In another implementation, the perfusion stents 402, 404 can be inserted into the DCD donor prior to cardiac death and then are deployed at the time of cardiac death. In yet another implementation, the apparatus can be inserted and deployed in a donor who expires prematurely before a donor team is ready to perform the explant procedure. In any case, during the period of time before explant can be performed, the perfusion fluid reduces warm ischemia time and preserves organ function.

Figure 18:
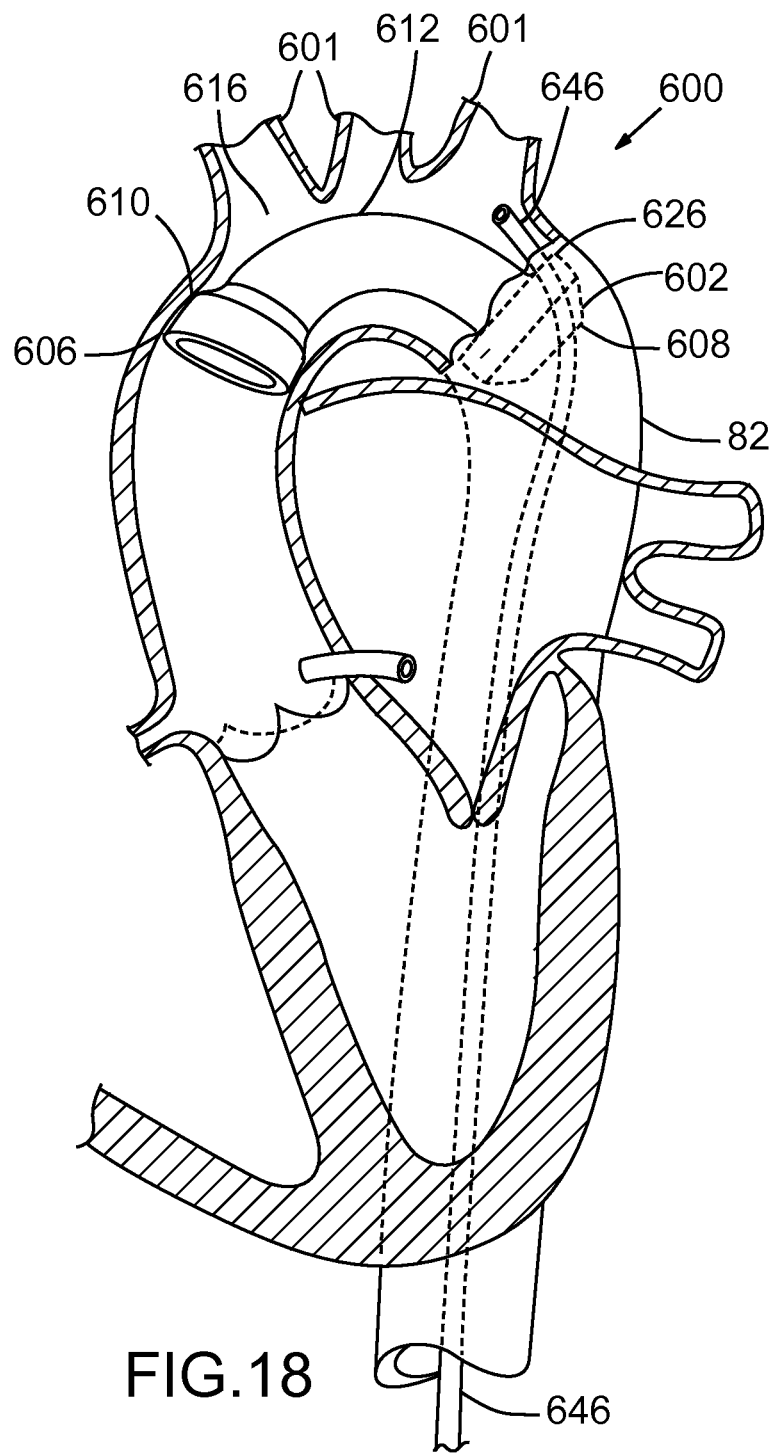
FIG. 18 illustrates an exemplary embodiment of an endovascular apparatus for perfusing organs of a patient, according to another embodiment.

FIG. 18 shows an endovascular apparatus 600, according to another embodiment. The endovascular apparatus 600 is similar in many respects to the apparatus 400 of FIGS. 10 and 11, but has been modified for deployment in the aortic arch and superior vena cava to isolate and perfuse the head and arms of a patient with a perfusion fluid.

The apparatus 600 in the illustrated embodiment comprises an arterial perfusion stent 602 and a venous perfusion stent (not pictured). The arterial perfusion stent 602 is configured for deployment in the aortic arch and to isolate blood to the head and arms via carotid and subclavian arteries 601. When deployed in a patient, the endovascular apparatus 600 allows blood from the heart to pass uninterrupted through a central lumen of the arterial perfusion stent 602 and flow via the aorta 82 to perfuse the abdomen and lower body and then flow uninterrupted through the inferior vena cava to return to the heart. Further, the arterial perfusion stent 602 of endovascular apparatus 600 is configured to introduce a perfusion fluid (e.g., re-oxygenated and/or warmed blood) into the carotid and subclavian arteries 601 for the purpose of perfusing the head and arms with the perfusion fluid. For example, the apparatus 600 can be used to maintain blood flow to the brain or spinal cord during a surgical procedure that restricts such flow in order to reduce or prevent brain ischemia or spinal cord ischemia during the procedure.

The arterial perfusion stent 602 can have a similar construction as that of the arterial perfusion stent 402. The size and shape of the arterial perfusion stent 602 can be generally similar to the size and shape of the arterial perfusion stent 402, with modifications as needed to allow for deployment of the arterial perfusion stent 602 in the aortic arch. For example, similar to arterial perfusion stent 402, the arterial perfusion stent 602 comprises an elongated body that includes an annular frame supporting a non-porous liner that can be radially compressible to a compressed state for delivery through the body to a deployment site and expandable to its functional size shown in FIG. 18 at the deployment site. Similar to perfusion stent 402, the perfusion stent 602 can be self-expanding, or, in other embodiments, can be a plastically-expandable perfusion stent. The frame and the non-porous liner of the arterial perfusion stent 602 can be made of the same materials as those used for the arterial perfusion stent 402.

The stent 602 defines a central lumen that extends from a proximal end 608 to a distal end 606 of the perfusion stent. The central lumen allows passage of fluid (e.g., blood) through the body of the perfusion stent, thus maintaining blood flow through the artery in which the perfusion stent is deployed. In the radially expanded state of the perfusion stent, distal and proximal end portions 610, 614 have an outer diameter that is larger than the outer diameter of an intermediate portion 612, thereby defining an annular perfusion space 616 between the end portions and around the intermediate portion. The outer surfaces of the distal and proximal end portions 610, 614 form a seal against the inner wall of the aorta when the arterial perfusion stent is in the radially expanded state.

Similar to the arterial perfusion stent 402, the arterial stent 602 can comprise a perfusion lumen (such as defined by an arterial perfusion conduit or sleeve 646) that is in fluid communication with the arterial perfusion space 616 and facilitates perfusion of blood or fluid through the head and arms, while allowing normal blood flow between the heart and lower extremities. The perfusion fluid can flow through the perfusion lumen and into the arterial perfusion space 416. The arterial perfusion conduit 646 can extend at least partially through the proximal end portion 614 of the stent body and has a proximal end that can extend beyond the proximal end portion 614, where it can be fluidly connected to a catheter that extends outside of the body of the patient. Desirably, the catheter can be connected to an oxygenator and/or blood warmer and/or a blood pump to treat and pump the blood of the patient as needed.

The venous perfusion stent included in the apparatus 600 can be configured for deployment in the superior vena cava to isolate blood flow returning from the head and arms to the heart via the superior vena cava. The venous perfusion stent is configured to receive the perfusion fluid from the superior vena cava that was introduced into the body from the arterial perfusion stent 602. The venous perfusion stent of apparatus 600 can have a structure similar to the venous perfusion stent of apparatus 400, and can be configured for placement in the superior vena cava in any way so as to collect fluid returning via the superior vena cava to the heart. In some non-limiting embodiments the venous stent can include a configuration such that a perfusion space of the stent collects fluid (e.g., blood) from the right brachiocephalic vein, the left internal jugular, or the right brachiocephalic vein and the left internal jugular.

Once the arterial and venous perfusion stents of the apparatus 600 are in place, the proximal and distal end portions of each stent form a seal against the inner walls of the aortic arch and superior vena cava, respectively, thereby isolating blood flow from the aorta to the carotid and subclavian arteries 601 and from the veins of the head and arms to the superior vena cava. Thus, blood flow to and from the head and arms is redirected from the superior vena cava through a venous perfusion conduit to a blood pump, blood oxygenator and/or warmer that are outside the patient's body. The blood is then redirected back into the patient via the catheter 646 connected to the arterial perfusion conduit 646 and into the arterial perfusion space 616 around the arterial perfusion stent 602. The blood flows through the carotid and subclavian arteries 601 to the head and arms, and back to superior vena cava.

The embodiments disclosed herein can be used for procedures other than procedures for preserving organ function for explant surgery. For example, in another implementation, an endovascular apparatus (e.g., an apparatus of FIG. 1, 5, 6, 10, 11, 12, or 18) can be used to perfuse organs during survival surgery, such as cardiac or proximal aortic repairs where prolonged cessation of blood flow poses a risk of organ damage. In another implementation, an endovascular apparatus (e.g., an apparatus of FIG. 1, 5, 6, 10, 11, 12, or 18) can be used to selectively perfuse organs, but not other body regions, with a therapeutic agent. For example, if a particular therapeutic agent has therapeutic effect on the organs, but is toxic to other body regions (for example, the central nervous system), the agent can be selectively administered to the organs using a disclosed endovascular apparatus. In one non-limiting example, a chemotherapeutic agent can be delivered to the visceral organs using a disclosed endovascular apparatus (e.g., an apparatus of FIG. 1, 5, 6, 10, 11, or 12) to selectively perfusion the visceral organs of the body with a solution (e.g., blood) that includes the chemotherapeutic agent.

General Considerations

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an" and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C" or "A, B and C."

As used herein, the term "coupled" generally means physically coupled or linked and does not exclude the presence of intermediate elements between the coupled items absent specific contrary language.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of perfusing organs in a patient's body, the method comprising:
   isolating the visceral arteries and the visceral veins from blood circulating through the patient's heart;
   perfusing the visceral arteries, the visceral veins, and the abdominal organs with a perfusion fluid that is fluidly separated from the blood circulating through the patient's heart;
   while the visceral arteries and the visceral veins are isolated and the visceral arteries, the visceral veins, and the abdominal organs are being perfused, allowing the patient's blood to continue to circulate through the heart.

2. The method of claim 1, wherein the act of perfusing the visceral arteries, the visceral veins, and the abdominal organs comprises establishing a flow of the perfusion fluid that flows into and through an arterial catheter placed in the patient's aorta, into and through the visceral arteries, the abdominal organs, and the visceral veins, and into and through a venous catheter placed in the patient's vena cava.

3. The method of claim 2, wherein:
   isolating the visceral arteries comprises inflating balloons on the arterial catheter to seal the balloons against the aorta wall upstream and downstream of the visceral arteries; and isolating the visceral veins comprises inflating balloons on the venous catheter to seal the balloons against the vena cava wall upstream and downstream of the visceral veins.

4. The method of claim 2, wherein the act of allowing the patient's blood to continue to circulate through the heart comprises shunting blood from the heart to flow into and through the arterial catheter, through a blood warmer, into and through the venous catheter, and back into the vena cava.

5. The method of claim 4, wherein:
blood from the heart flows through a first lumen in the arterial catheter and through a first lumen in the venous catheter; and
the perfusion fluid flows through a second lumen in the arterial catheter, outwardly through side openings in the arterial catheter, inwardly through side openings in the venous catheter, and through a second lumen in the venous catheter.

6. The method of claim 4, further comprising:
placing a first conduit into an artery of a lower extremity of the patient;
placing a second conduit into a vein of a lower extremity of the patient;
shunting a portion of blood from the arterial catheter to flow into and through the first conduit, into and through the vasculature of the patient's lower extremities, into and through the second conduit, and back into the venous catheter.

7. The method of claim 1, wherein the perfusion fluid comprises a cold perfusion solution at a temperature of 4 degrees C. to 6 degrees C.

8. The method of claim 7, wherein the perfusion solution comprises one or more of heparin, pentastarch, steroids, lactobionic acid, magnesium sulfate, raffinose, adenosine, allopurinol, glutathione, and potassium hydroxide.

9. The method of claim 1, wherein the perfusion fluid comprises blood.

10. The method of claim 9, wherein the blood being used as the perfusion fluid flows outside the body, is warmed and oxygenated, and then pumped back into the body.

11. The method of claim 1, wherein the act of allowing the patient's blood to continue to circulate through the heart comprises shunting blood from the heart to flow into and through an arterial catheter placed in the patient's aorta, through a blood warmer, into and through a venous catheter placed in the patient's vena cava, and back into the vena cava.

12. The method of claim 1, further comprising performing an explant procedure on the patient.

13. The method of claim 1, wherein the act of isolating the visceral arteries and the visceral veins from blood circulating through the patient's heart comprises deploying a first perfusion stent in the patient's aorta and a second perfusion stent in the patient's vena cava, the first perfusion stent allowing blood from the heart to flow in a downstream direction from a location upstream of the abdominal organs to a location downstream of the abdominal organs without flowing into the visceral arteries, the second perfusion stent allowing blood in the vena cava to flow in a downstream direction from a location upstream of the abdominal organs to a location downstream of the abdominal organs without mixing with blood from the visceral veins.

14. The method of claim 13, the act of perfusing the visceral arteries, the visceral veins, and the abdominal organs comprises establishing a flow of the perfusion fluid that flows into and through a first perfusion conduit having an outlet opening in communication with the visceral arteries, into and through the visceral arteries, the abdominal organs, the visceral veins, and into and through a second perfusion conduit having an inlet opening in communication with the visceral veins.

15. The method of claim 14, wherein:
the first perfusion stent has enlarged end portions sealed against the inner wall of the aorta and an intermediate portion defining an arterial perfusion space between the inner wall of the aorta and the outer surface of the intermediate portion, the second perfusion stent has enlarged end portions sealed against the inner wall of the vena cava and an intermediate portion defining a venous perfusion space between the inner wall of the vena cava and the outer surface of the intermediate portion; and
the perfusion fluid flows through the first perfusion conduit, through the arterial perfusion space, through the visceral arteries, through the abdominal organs, through the visceral veins, through the venous perfusion space, and into the second perfusion conduit, in that order.

16. The method of claim 15, wherein:
the first perfusion conduit has an end portion that extends through one of the enlarged end portions of the first perfusion stent; and
the second perfusion conduit has an end portion that extends through one of the enlarged end portions of the second perfusion stent.

17. A method of perfusing organs in a patient's body, the method comprising:
inserting an arterial catheter into the patient's aorta, the arterial catheter having a first lumen, a second lumen, and first and second balloons spaced apart along the length of the arterial catheter;
positioning the arterial catheter in the aorta such that the first balloon is upstream of the visceral arteries and the second balloon is downstream of the visceral arteries;
inserting a venous catheter into the patient's vena cava, the venous catheter having a first lumen, a second lumen, and first and second balloons spaced apart along the length of the venous catheter;
positioning the venous catheter in the vena cava such that the first balloon is upstream of the visceral veins and the second balloon is downstream of the visceral veins;
inflating the first and second balloons of the arterial and venous catheters, thereby isolating the visceral arteries and visceral veins from blood circulating through the patient's heart;
establishing a flow of a perfusion fluid that flows into and through the second lumen of the arterial catheter, into and through the visceral arteries, the abdominal organs, and the visceral veins, and into and through the second lumen of venous catheter; and
allowing blood from the heart to flow into and through the first lumen of the arterial catheter, and back into and through the first lumen of the venous catheter.

18. The method of claim 17, wherein:
the arterial catheter comprises one or more side openings located between the balloons of the arterial catheter and perfusion fluid in the second lumen of the arterial catheter flows outwardly through the side openings and into the visceral arteries; and
the venous catheter comprises one or more side openings located between the balloons of the venous catheter and perfusion fluid in the visceral veins flows inwardly through the side openings of the venous catheter and into the second lumen of the venous catheter.

19. The method of claim 17, wherein blood from the first lumen of the arterial catheter flows through a blood warmer before it is returned to the first lumen of the venous catheter.

20. The method of claim 17, wherein the perfusion fluid comprises a heparin solution.

21. The method of claim 17, wherein the perfusion fluid comprises blood.

22. An assembly for perfusing organs in a patient's body, the assembly comprising:
    an arterial catheter configured to be inserted into the aorta of a patient, the arterial catheter comprising a first lumen, a second lumen, and first and second balloons spaced apart along the length of the arterial catheter, the balloons being configured to seal against the inner wall of the aorta upstream and downstream of the visceral arteries to isolate the visceral arteries from blood circulating through the patient's heart;
    a venous catheter configured to be inserted into the vena cava of a patient, the venous catheter comprising a first lumen, a second lumen, and first and second balloons spaced apart along the length of the venous catheter, the balloons being configured to seal against the inner wall of the vena cava upstream and downstream of the visceral veins to isolate the visceral veins from blood circulating through the patient's heart;
    a source of a perfusion fluid in fluid communication with the second lumen of the arterial catheter; and
    wherein the first lumen of the arterial catheter is in fluid communication with the first lumen of the venous catheter to allow blood from the heart to flow into and through the first lumen of the arterial catheter, and back into and through the first lumen of the venous catheter.

23. The assembly of claim 22, wherein:
    the arterial catheter comprises one or more side openings located between the balloons of the arterial catheter such that perfusion fluid in the second lumen of the arterial catheter can flow outwardly through the side openings and into the visceral arteries; and
    the venous catheter comprises one or more side openings located between the balloons of the venous catheter such that perfusion fluid in the visceral veins can flow inwardly through the side openings of the venous catheter and into the second lumen of the venous catheter.

24. The assembly of claim 22, further comprising a blood warmer that is fluid communication with the first lumen of the arterial catheter and the first lumen of the venous catheter.

25. The assembly of claim 22, further comprising:
    a first conduit that can shunt a portion of the blood from the first lumen of the arterial catheter to flow into the lower extremities of the patient; and
    a second conduit that can receive the portion of blood from the lower extremities and return it to the first lumen of the venous catheter.

26. An assembly for perfusing organs in a patient's body, the assembly comprising:
    a first perfusion stent configured to be deployed within the aorta of a patient, the first perfusion stent having a lumen allowing blood from the heart to flow in a downstream direction from a location upstream of the abdominal organs to a location downstream of the abdominal organs, the lumen of the first perfusion stent being fluidly isolated from the visceral arteries;
    a second perfusion stent configured to be deployed within the vena cava of the patient, the second perfusion stent having a lumen allowing blood to flow in a downstream direction from a location upstream of the abdominal organs to a location downstream of the abdominal organs, the lumen of the second stent being fluidly isolated from visceral veins;
    a source of a perfusion fluid;
    a first perfusion conduit having an inlet in fluid communication with the source of the perfusion fluid and an outlet that is configured to be in fluid communication with the visceral arteries when the first perfusion stent is deployed within the aorta; and
    a second perfusion conduit having an inlet that is configured to be in fluid communication with the visceral veins when the second perfusion stent is deployed within the vena cava.

27. The assembly of claim 26, wherein the second perfusion conduit has an outlet in fluid communication with the source of the perfusion fluid such that the perfusion fluid can re-circulate through the first perfusion conduit, through the visceral arteries, through the abdominal organs, through the visceral veins, and through the second perfusion conduit.

28. The assembly of claim 27, wherein the source of the perfusion fluid comprises a blood pump and oxygenator.

* * * * *